United States Patent [19]
Zähringer et al.

[11] Patent Number: 5,798,343
[45] Date of Patent: Aug. 25, 1998

[54] 7-O-CARBAMOYLHEPTOSE DERIVATIVES, PROCESS FOR THEIR PRODUCTION AND THEIR USE IN TREATING PSEUDOMONAS INFECTIONS

[75] Inventors: Ulrich Zähringer; Frank Beckmann; Hermann Moll, all of Borstel, Germany

[73] Assignee: Forschungsinstitut Borstel Institut fur Experimentelle Biologie und Medizin, Borstel, Germany

[21] Appl. No.: 765,970

[22] PCT Filed: Jul. 14, 1995

[86] PCT No.: PCT/EP95/02780

§ 371 Date: Jan. 15, 1997

§ 102(e) Date: Jan. 15, 1997

[87] PCT Pub. No.: WO96/02550

PCT Pub. Date: Feb. 1, 1996

[30] Foreign Application Priority Data

Jul. 15, 1994 [DE] Germany .................. 44 25 098.3

[51] Int. Cl.[6] .................. A61K 31/735; A61K 31/70; C07H 1/00; C07H 13/12
[52] U.S. Cl. .................. 514/54; 514/23; 514/25; 536/1.11; 536/4.1; 536/17.2; 536/123.1
[58] Field of Search .................. 536/17.2, 1.11, 536/4.1, 123.1; 514/23, 25, 54

[56] References Cited

PUBLICATIONS

Gerald P. Bodey et al., "Infections Caused by Pseudomonas Aeruginosa", Reviews of Infectious Diseases, vol. 5 No. 2, pp. 279–313, Mar.–Apr., 1983.

U. Winkler et al., "Pseudomonas Aeruginosa Infections of the Respiratory Tract in Cystic Fibrosis Patients", Klinische Wochen–Schrift, vol. 63, pp. 490–498, 1985.

Norberto J. Palleroni, "Pseudomonas Classification", Antonie Van Leenwenhoek, vol. 64, pp. 231–251, 1993.

Andrew M. Kropinski et al., "Structure and Functions of Pseudomonas Aeruginosa Lipopolysaccharide", Antibiot. Chemother., vol. 36, pp. 58–73, 1985.

Robert E.W. Hancock et al., "Molecular Organization and Structural Role of Outer Membrane Macromolecules," Bacterial Cell Wall, chapter 12, pp. 263–279, 1994.

N.K. Kochetkov et al., "The Structures of O–Specific Polysaccharides of Bacterium Pseudomonas Aeruginosa", Soviet Scientific Reviews B. Chem., vol. 13, pp. 1–101, 1989.

F.E. Di Padova et al., "A broadly Cross–Protective Monoclonal Antibody Binding to *Escherichia coli* and Salmonella Lipopolysaccharides", Infection and Immunity, vol. 61 No. 9, pp. 3863–3872, Sep., 1993.

Peter S.N. Rowe et al., "Structure of the Core Oligosaccharide from the Lipopolysaccharide of Pseudomonas Aeruginosa PAC1R and Its Defective Mutants", Euro. Biochem. 132, pp. 329–337, 1983.

Eleonora Altman et al., "A Novel Approach to the Structure Elucidation of the Core Region of the Lilpopolysaccharide from Pseudomonas Aeruginosa 06 (HABS) Rough–Type Mutant R5", XVIth Inter. Carbohydrate Symposium, p. 626, Jul. 5–10, 1992.

E. Altman et al., "A Novel Approach to the Structure Elucidation of the Core Region of Lipopolysaccharides. Structure of the Pseudomonas Aeruginosa 06 (Habs) LPS Core Oligosaccharide.", 2nd Conference of the Intern. Endotoxin Society, p. 55, Aug. 18, 1992.

William F. McManus, M.D., F.A.C.S., et al., "Burn Wound Infection", The Journal of Trauma, vol. 21 No. 9, pp. 753–756, Sep., 1981.

*Primary Examiner*—Gary L. Kunz
*Attorney, Agent, or Firm*—Browdy and Neimark

[57] ABSTRACT

The invention describes 7-O-carbamoyl heptose derivatives of general formula (I) in which R is the substituent $R^1$ or a group of general formula (II) in which $R^1$ is a hydrogen atom, a methyl group or a suitable linker substituent suitable for a covalent coupling, a process for their production and their use in producing reagents and compositions for the diagnosis and therapy of pseudomona infections in humans and animals, and a screening process for their detection in Gram-negative bacteria.

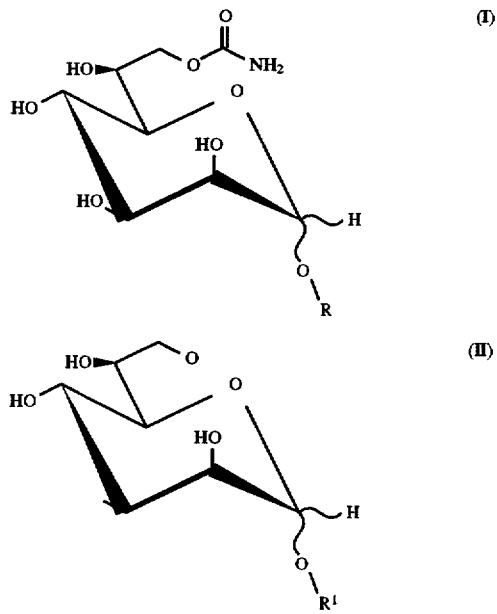

6 Claims, 36 Drawing Sheets

(COMPOUND NO. 4)
M=434

(COMPOUND NO. 5)
M=435

(COMPOUND NO. 3)
M=351

(COMPOUND NO. 12)
M=599

(COMPOUND NO. 6)
M=369

(COMPOUND NO. 8)
M=322

(COMPOUND NO. 14)
M=570

(COMPOUND NO. 16)
M = 424

(COMPOUND NO. 15)
M=395

(COMPOUND NO. 18)
M-395

(COMPOUND NO. 17)
M=452

$M = C_{16}O_{14}H_{29}N = 459.4$
$Na = 23.0$
$M + Na = 482.4$

7-O-CARBAMOYLHEPTOSE DERIVATIVES, PROCESS FOR THEIR PRODUCTION AND THEIR USE IN TREATING PSEUDOMONAS INFECTIONS

This case is filed under 35 USC 371 as the U.S. atage of PCT/EP95/02780 filed Jul. 14, 1995.

AREA OF THE INVENTION

The present invention relates to 7-O-carbamoylheptose derivatives, to a process for their production and to their use for the production of reagents and compositions for the diagnosis and therapy of pseudomonas infections in humans and animals, and to a screening process for their determination in Gram-negative bacteria.

BACKGROUND OF THE INVENTION

Bacteria of the Pseudomonadaceae family are Gram-negative organisms which occur ubiquitously and whose pathogenicity for humans is normally very weakly developed. P. aeruginosa, by contrast, is a human-pathogenic species and occurs frequently in wound infections and there especially as secondary infection in cases of higher-degree burns of the skin, and in cases of suppurative otitis media. In immunocompromised patients and in cases of cystic fibrosis it is particularly the antibiotic-resistant pseudomonads which are of outstanding medical importance [McManus et al., J. Trauma 21 (1981) 753–763, Bodey et al., Rev. Inf. Dis., 5 (1983), 279–313, Winkler et al., Klin. Wochenschrift, 63 (1985) 490–498].

In terms of taxonomy, pseudomonads comprise a very heterogeneous family. Their species-related heterogeneity represents a considerable impediment to the medical diagnosis and therapy of pseudomonas infections. This is why it was only recently proposed that this family of Pseudomonadaceae be divided into five different subgroups [N. J. Palleroni, Antonie Van Leeuwenhoek, 64 (1993) 231–251]. The first group (RNA group 1) includes P. aeruginosa, P. fluorescens and P. putida. The second group (RNA group 2) comprises the pseudomonads which are pathogenic for plants and animals (for example P. plantarii) and is now referred to as burkholderia. Finally, a distinction is also made between comamonas (group 3) and the purple bacteria (group 4) which continue to be referred to as "pseudomonas" (for example P. diminuta, P. vesicularis) and lastly also xanthomonas (RNA group 5).

Beyond this, pseudomonads are also of biomedical interest for other reasons. They are extremely resistant to antibiotics [A. M. Kropinski et al., Antimicrob. Agents Chemother., 36 (1985) 58–73]. There is evidence that this antibiotic resistance is associated with the structure of the cell wall membrane, that is to say with a high density of negatively charged phosphate groups on molecules in the outer cell wall membranes [R. E. W. Hancock et al., in: Bacterial Cell Wall, J. M. Ghuysen and R. Hakenbeck (eds.), Elsevier Amsterdam, 1994, 263–279). Such surface structures are in all Gram-negative bacteria essentially integral proteins of the cell membrane (OMP, porins) and the lipopolysaccharide (LPS, endotoxin). These molecules represent antigens which show high genus-, species- and subspecies-specific immunogenicity and, during the course of an infection, induce serotype-specific antibodies which may be of great importance to both diagnosis and therapy.

Over the course of the last decade it has been possible to acquire considerable knowledge about the serological and biological properties of these antigens. There has also been intensive study and elucidation of the LPS structures and there particularly of their immunogenic outer components (O chains) of the 17 serotypes now known. There has been complete chemical analysis of all P. aeruginosa O chains, and some of them have also been synthesized and classified serologically into various immunotypes (Fischer) and serotypes (Lanyi, Habs) [N. K. Kochetkov and Yu. A. Knirel, Sov. Sci. Rev. B. Chem. 13 (1989) 1–101]. Based on this structural knowledge, various P. aeruginosa serotyping kits with monoclonal antibodies have been produced and are still commercially available. The disadvantage of these antibody test cocktails is that they detect only the known antibodies, but all monoclonal O-specific antibodies are necessary in order to detect all O types.

Besides the antigenic assay processes which have been known for a long time for the immunologically highly specific O chains, there has recently been development of cross-reacting monoclonal antibodies whose epitope is located not in the highly variable O chain of the lipopolysaccharide but in the less variable core oligosaccharide. Since these structures make essential contributions to the function of the outer cell membrane, core oligosaccharides are regarded rather as conservative structural elements of the immunogenic LPS, against which it might be possible to produce broadly cross-protecting antibodies. This has recently been experimentally demonstrated for the first time. A mouse monoclonal antibody (MAb) whose specificity was directed against the core region showed broad cross-reactivity and broad cross-protection for all five Escherichia coli (R1, R2, R3, R4, K-12) and for the Salmonella minnesota core oligosaccharide structure, irrespective of the structure of the O chain of the particular LPS [Di Padova et al., Infect. Immun. 61 (1993) 3863–3872]. This MAb (WN1 222-5) of the IgG2a class confers broad cross-protection against S. minnesota and E. coli endotoxin but not against P. aeruginosa or Klebsiella pneumoniae. The reason for this is ascribed to the different core oligosaccharide structure. The core oligosaccharide structures of P. aeruginosa and K. pneumoniae have hitherto been analysed only incompletely or are substantially unknown.

In a study in which various rough form mutants of P. aeruginosa were produced and their core oligosaccharide was chemically investigated [P. S. N. Rowe & P. M. Meadow, Eur. J. Biochem. 132 (1983) 329–337], the first proposed structures of the core region were published. One structural pecularity was the presence of the amino acid alanine (Ala) in the outer core oligosaccharide of all the P. aeruginosa rough form mutants investigated. This proposed structure was not revised and improved until ten years later, on a P. aeruginosa mutant [R5 (Habs 06)] by $^1$H-NMR spectroscopy [E. Altman et al., Int. Carb. Conference, Paris 1992, E. Altman et al., 2nd IES Conference, Vienna 1992].

However, very recent investigations in our laboratory have revealed that even this structure of the core oligosaccharide of the deep rough mutants [R5 (Habs 06(] derived from the rough form mutants PAC1R of P. aeruginosa is still incomplete. It was initially known that this core region is extensively phosphorylated. On the other hand, the degradation methods and analytical processes used by E. Altman et al. were essentially unsuitable to allow the 7-O-carbamoyl-L-glycero-D-manno-heptopyranose which is described in detail for the first time according to the present invention to be identified and analyzed by spectrometry ($^1$H-NMR).

SUMMARY OF THE INVENTION

The inventors have investigated the chemical structure of the lipopolysaccharide of pseudomonads with the aim of providing specific mono- and disaccharides which can be employed as serological markers in the diagnosis and therapy of pseudomonas infections.

In these investigations it was possible to analyze and completely characterize the chemical structure of a previously unknown 7-O-carbamoyl-L-glycero-D-mannoheptopyranose in the core oligosaccharide of the LPS of pseudomonads of RNA group 1. It has not been possible to find this heptopyranose in other Gram-negative bacteria apart from pseudomonads of RNA group 1 (for example in all Enterobacteriaceae).

The invention therefore relates to 7-O-carbamoylheptose derivatives of the general formula (I)

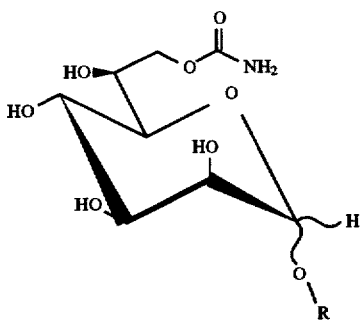

in which R is the substituent $R^1$ or a group of the general formula (II)

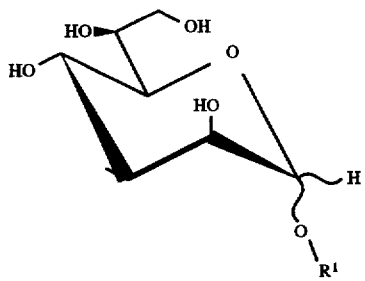

in which $R^1$ is a hydrogen atom, a methyl group or a linker substituent suitable for a covalent coupling.

The invention furthermore relates to a process for the production of the 7-O-carbamoylheptose derivatives which is characterized in that a lipopolysaccharide of pseudomonads of RNA group 1 is created with hydrofluoric acid, the resulting product is dialysed against water until a neutral pH is reached, the lipopolysaccharide which has been dephosphorylated in this way is methanolyzed, and subsequently a permethylation or peracetylation is carried out, the resulting 7-O-carbamoylheptose derivatives are fractionated by liquid chromatography (checking the purity by gas-liquid chromatography or combined gas-liquid chromatography/mass spectrometry) and, if required, the substituent $R^1$ is introduced into the resulting 7-O-carbamoylheptose derivatives by a process known per se.

The invention furthermore relates to a screening process for determining the 7-O-carbamoylheptose derivatives in Gram-negative bacteria, which is characterized in that intact bacteria are treated, without previous removal of the lipopolysaccharide, with hydrofluoric acid, then hydrolyzed or methanolyzed to liberate the heptose derivatives, and subsequently a permethylation is carried out and the permethylated product is analyzed by gas-liquid chromatography or combined gas-liquid chromatography/mass spectrometry.

The 7-O-carbamoylheptose derivatives of the general formula (I) can be used to produce reagents and compositions for the diagnosis and therapy of pseudomonas infections in humans and animals.

DETAILED DESCRIPTION OF THE PREFERRED EMBODIMENTS

The linker substituent indicated by $R^1$ in the general formula (II) is preferably a cysteamine residue, an allyl group or a straight-chain or branched-chain $C_{1-18}$-alkyl group which may contain a terminal hydroxyl, amino, acyl, carboxyl or allyl group. $R^1$ is preferably a hydrogen atom or a methyl group.

The present invention has succeeded in making the heptose region in the core oligosaccharide of the LPS of pseudomonads of biomedical importance available for analysis and in complete characterization of the phosphate-free structure thereof. Furthermore, the invention has succeeded in making it possible to isolate this previously unknown sugar from these bacteria and to analyze and quantify it by combined gas chromatography/mass spectrometry (GC-MS).

It has been possible to date to identify the novel 7-O-carbamoylheptopyranose only in pseudomonads of RNA group 1 (especially in the human-pathogenic *P. aeruginosa* and in *P. fluorescens*).

Furthermore, the novel sugar occurs in the LPS of all immunotypes of *P. aeruoginosa* (Fischer 2.7), investigated to date, irrespective of the structure of the O chain. No exceptions to this rule are known as yet. The 7-O-carbamoylheptopyranose does not occur in the LPS of pseudomonads which are pathogenic to plants (for example *P. plantarii*), which are now assigned to burkholderia, no longer to the group of pseudomonads.

Both the diagnostic and taxonomic significance of the 7-O-carbamoylheptopyranose can be deduced from these findings. The 7-O-carbamoylheptopyranose is likewise absent from all other Gram-negative bacteria investigated to date: *Klebsiella pneumoniae*, K25; *Yersinia enterocolitica*, mutant 490 M; *Campylobacter jejuni* RN 16 0:58; CCUG 10936; *Proteus mirabilis*, mutant $R_{45}$; *Haemophilus influenzae*, B, strain Eagan, *Vibrio parahaemolyticus*, serotype 012, *Salmonella minnesota*, SF 1111, and *E. coli* O111 were negative for the 7-O-carbamoylheptose in the screening process, which underlines once again the diagnostic importance of this newly discovered sugar.

Using the sugar according to the invention it has now become possible further to improve the species-specific diagnosis of pseudomonads and their taxonomic classification.

Since it is known that monoclonal antibodies directed against epitopes of the inner and outer core regions are able also to recognize wild-type LPS with analogous core oligosaccharides [Di Padova, F. et al., *Infect. Immun.*, 61 (1993) 3863–3872 and Rietschel, e.Th. et al., FASEB. J., 8 (1994) 217–225], it is possible on the basis of the present structure elucidation to define species-specific epitopes by means of monoclonal antibodies which cruccially simplify and improve the serodiagnosis of these human-pathogenic organisms. This serodiagnosis can at present be carried out only via the O-specific chain, with the known disadvantages of lacking cross-specificities.

The pseudomonads employed in the process according to the invention, which occur in soil, water, waste water, on plants and in foodstuffs, are extremely well-known microorganisms which can also be obtained from recognized depositary authorities.

Depending on the conditions used for the methanolysis, it is possible by the process according to the invention to produce either the heptose monosaccharide or the heptose di- or oligosaccharide (see also Example 3.1 hereinafter).

EXAMPLE

Figure 1A:
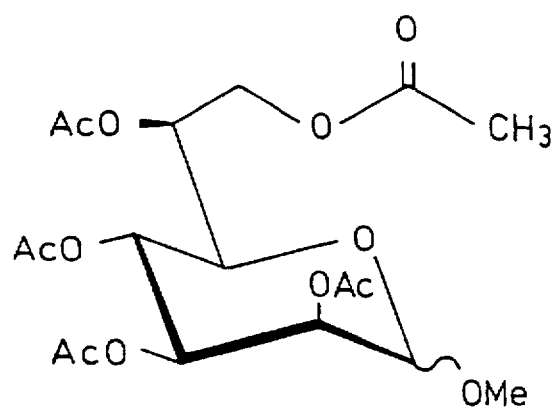
FIG. 1 shows the structural formula, the electron impact mass spectrum (1) and the Cl—|NH$_3$| mass spectrum (2) of methyl-2,3,4,6,7-penta-O-acetyl-D-glycero-α/β-D-manno-heptopyranose (compound No. 4).

The compounds mentioned hereinafter have the following structural formulae in which Me=methyl and Ac=acetyl.

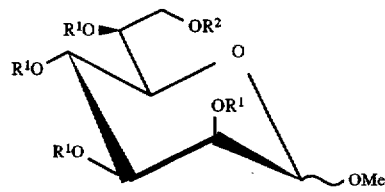

| Compound No. 1: | 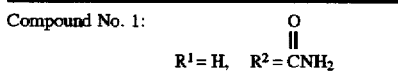 |
| --- | --- |
| | $R^1 = H$, $R^2 = CNH_2$ |
| Compound No. 2: | $R^1 = R^2 = H$ |
| Compound No. 3: | 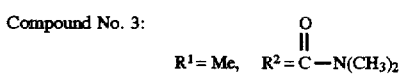 |
| | $R^1 = Me$, $R^2 = C—N(CH_3)_2$ |
| Compound No. 4: | $R^1 = R^2 = Ac$ |
| Compound No. 5: | 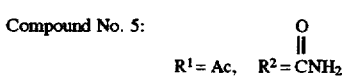 |
| | $R^1 = Ac$, $R^2 = CNH_2$ |
| Compound No. 6: | 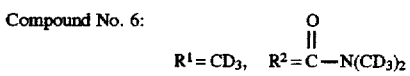 |
| | $R^1 = CD_3$, $R^2 = C—N(CD_3)_2$ |
| Compound No. 7: | $R^1 = Me$, $R^2 = H$ |
| Compound No. 8: | $R^1 = Me$, $R^2 = Ac$ |

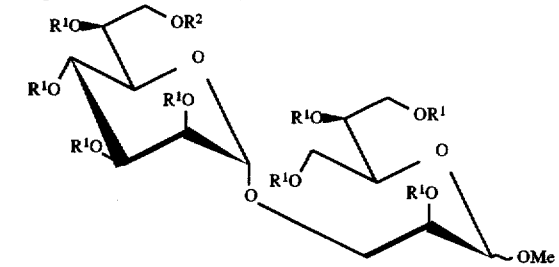

| Compound No. 9: | 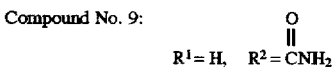 |
| --- | --- |
| | $R^1 = H$, $R^2 = CNH_2$ |
| Compound No. 10: | $R^1 = R^2 = H$ |
| Compound No. 11: | 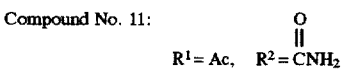 |
| | $R^1 = Ac$, $R^2 = CNH_2$ |
| Compound No. 12: | 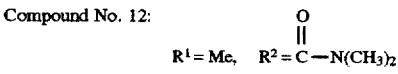 |
| | $R^1 = Me$, $R^2 = C—N(CH_3)_2$ |
| Compound No. 13: | $R^1 = Me$, $R^2 = H$ |
| Compound No. 14: | $R^1 = Me$, $R^2 = Ac$ |

-continued

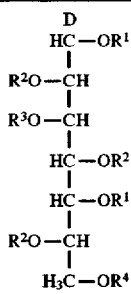

Compound No. 15: $R^1 = R^4 = Ac$, $R^2 = R^3 = Me$

Compound No. 16:
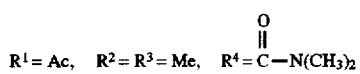
$R^1 = Ac$, $R^2 = R^3 = Me$, $R^4 = C-N(CH_3)_2$ (with =O)

Compound No. 17:
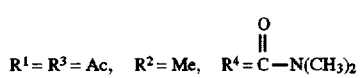
$R^1 = R^3 = Ac$, $R^2 = Me$, $R^4 = C-N(CH_3)_2$ (with =O)

Compound No. 18: $R^1 = R^3 = Ac$, $R^2 = R^4 = Me$

Materials and Methods

Cultivation of bacteria and extraction of lipopolysaccharide

*Pseudomonas aeruginosa* bacteria (PAO, PAC605, PAC557 and R5 (Habs 06) were obtained from P. Meadow, University College, London, Great Britain [Rowe, P. S. N. and Meadow, P. M., Eur. J. Biochem., 132, (1983) 329–337] and from J. S. Lam, University of Guelph, Ontario, Canada [E. Altman, et al., *Biochemistry* 1994, submitted, E. Altman et al., Int. Carb. Conference, Paris 1992, E. Altman, et al., 2nd IES Conference Vienna 1992]. The PAO mutant is deposited at the Deutsche Sammlung von Mikroorganismen and Zellkulturen GmbH, Braunschweig, under number DSM 1707. The rough form mutant PAC 605 was cultivated in a 100 l fermenter, and the other *P. aeruginosa* mutants were cultivated in 2 l shake flask cultures as described [Kulshin, V. A. et al., *Eur. J. Biochem*, 198(1991) 697–704]. Lipopolysaccharides from the strains *P. aeruginosa* Fischer immunotypes 2 and 7 were obtained from Prof. B. Dmitriev, Moscow, *P. aeruginosa* 170519, 170520 and FH-N-845 were obtained from Prof. E. S. Stanislavsky, Moscow and *Pseudomonas plantarii* DSM 7128 originated from the DSM Deutsche Sammlung von Mikroorganismen und Zellkulturen GmbH, Braunschweig and *P. fluorescens* ATCC 49271 was obtained from the American Type Culture Collection, Rockville, Md., USA. All other LPS cargen: *Klebsiella pneumoniae*, K 25; *Yersinia enterocolitica*, mutant 490 M; *Campylobacter jejuni* RN 16 0:58; CCUG 10936; *Proteus mirabilis*, mutant $R_{45}$; *Haemophilus influenzae*, B, strain Eagan, *Vibrio parahaemolyticus*; serotype O12, *Salmonella minnesota*, SF 1111 (S form), and *E. coli* O111 (S form) originated from the LPS collection of the Forschungsinstitut Borstel.

The acquired heptose was prepared as mono- or oligomer using the *P. aeruginosa* PAC 605 mutant. To do this, dried bacteria (38.1 g) were washed with 1 liter each of ethanol, acetone and diethyl ether, and the ethereal sediment was dried (28.6 g, 75%). The membrane fraction obtained in this way underwent enzymatic digestion with DNAse (from bovine pancreas, Boehringer, Mannheim) and RNAse (bovine pancreas, Sigma) and proteinase K (from *Tritirachium album*, Boehringer). Extraction took place by a modified phenol/chloroform/petroleum method [PCP II (5 parts of phenol, 5 parts of chloroform, 8 parts of petroleum ether (boiling point 90°–100° C.) modified by Galanos et al., [Galanos, C., Lüderitz, O. and Westphal, O., *J. Biochem.*, 9, (1969), 245–249]. Exhaustive dialysis of distilled water was then carried out. The yield was 2.2 g (6%, m/m). Extraction of all other pseudomonas strains took place in an analogous manner by the method of Galanos et al. with yields of between 1 and 5%.

Gas chromatography (GC)

The analysis by gas chromatography was carried out with a Hewlett Packard gas chromatograph (model 5890, series II), equipped with a flame ionization detector (FID). Hydrogen was used as carrier gas with a column inlet pressure of 0.08 MPa. An SPB-5™ column (30 m, 0.25 mm ID, 0.25 µm film thickness, Supelco) which was operated with a temperature gradient (150° C. for 3 min, then 5° C./min to 330° C.) served as separation column. Evaluation was carried out using Hewlett Packard Chemstation Software® on a Vectra 486/66U.

Combined gas-liquid chromatography/mass spectroscopy (GC-MS) analysis

The combined gas-liquid chromatography/mass spectroscopy (GC-MS) was carried out with a Hewlett Packard HP 5989A MS engine which was equipped with an HP 5890 series II gas chromatograph and a capillary column (HP-5®, 30 m, 0.25 mm, 0.25 µ, Hewlett Packard). Electron impact mass spectra (EI-MS) were recorded with 70 eV. Ammonia was used as reactor gas for the chemical ionization mass spectrometry (CI-MS). The spectra were evaluated with a Hewlett Packard Chemstation Software® on a Vectra 486/66U.

NMR spectroscopy $^1$H-(360 MHz and $^{13}$C-(90 MHz) NMR spectra of the mono- and disaccharides were carried out using a Bruker NMR spectrometer (model AM-360) at room temperature in $D_2O$. The recording and processing of one-dimensional data and spectra with homo- ($^1$H,$^1$H-COSY) and heteronuclear ($^1$H,$^{13}$C-NMR) correlation took place using an ASPECT 3000 computer (Bruker) with the standard Bruker software DISNMR Version 89 11 01.0.

Laser desorption mass apectrometry (LD-MS)

The laser desorption mass spectrometry (LD-MS) was carried out using a Lamma 500 instrument (Leybol-Heraeus, Cologne) in the positive mode without addition of cationizing salts as described [B. Lindner et al., in: *Analytical Microbiology Methods*, (1990), Plenum Press New York, A. Fox, S. L. Morgan, L. Larsson and G. Odhan (eds.), pp. 149–161].

High pressure liquid chromatography (HPLC)

The high pressure liquid chromatography (HPLC) of the methylheptopyranose mono- and dimers (2α, 9α and 10α) was carried out in a DuPont system (pump 870, gradient controller 8800) on a Zorbax $NH_2$ column (9×250 mm). The column was operated with a $CH_3CN-H_2O$ gradient and a flow rate of 3.5 ml/min. The gradient for isolation of 9α consisted of eluent A [$CH_3CN-H_2O$ 925:75 (v/v)] and eluent B [$CH_3CN-H_2O$ 75:925 (v/v(]; 0% B-5 min-10% B-75 min-100% B-20 min-100% B]. The gradient for purification of 10α was [A: 92:8, (v/v)] and [B: 50:50, (v/v)]; 0% B-5 min-0% B-75 min-100% B-20 min-100% B]. Sugar components were detected in the eluate using a chiral detector (No. 1000A, Knauer) and were collected in fractions (3.5 ml) (Foxy, Colora). Aliquots of these fractions were additionally tested by thin-layer chromatography (TLC). The retention times under the specified conditions were 21 min (9α) and 40 min (2α) and 99 min (10α).

Thin-layer analysis (TLC)

The thin-layer analysis took place on silica gel 60 $F_{254}$ (Merck) aluminum plates in chloroform/methanol/water (100:100:30), v/v). The sugar derivatives were detected by spraying with 15% (v/v) $H_2SO_4$ in EtOH and subsequently heating.

Derivatization and degradation reactions
1. Dephosphorylation of the LPS

LPS (20 mg) was stirred with aqueous HF (48%) at 4° C. in a Teflon vessel overnight. It was subsequently dialyzed exhaustively with water until the pH reached neutrality. The inner dialyzate was lyophilized (12.2 mg, 61% m/m).

2. Liberation of the dephosphorylated core oligosaccharide

The dephosphorylated LPS (LPS-HF) was stirred in a sodium acetate buffer solution (0.1M NaOAc, pH 4.4) at room temperature for 8 h. The dephosphorylated core oligosaccharide was isolated after removal of lipoid A by centrifugation (20,000×g, 30 min) and subsequent Sephadex G-10 chromatography (2.5×120 cm) 7.2 mg, 59%, m/m, based on LPS-HF).

3. Production and derivatization of the methyl glycosides of the heptose mono- and oligomers 3.1 Production of the heptose methyl glycosides The dephosphorylated LPS (42 mg) was converted by treatment with HCl/MeOH into the methyl glycoside mono- and dimers. The monomers were produced by hydrolyzing in 2M HCl/MeOH at 85° C. for 30 min, and the oligomers were produced by hydrolyzing in 0.5M HCl/MeOH at 85° C. for 30 min, and were isolated by HPLC (Zorbax-NH$_2$). Yield of monomer (1, 1.4 mg) and dimer (9α, 2.2 mg)

3.2. Derivatization of the heptose methyl glycosides 3.2.1 Peracetylation

The methyl glycosides (1.5 mg) produced as in 3.1 were derivatized with acetic anhydride/pyridine (Ac$_2$O/pyridine) at 37° C. for 30 min and subsequently analyzed by a GC-MS. Deuterium-labeled peracetylated heptose derivatives were produced in an analogous manner by derivatization with (CD$_3$CO)$_2$O/pyridine.

3.2.2. Permethylation

The heptoses and the dephosphorylated core oligosaccharide (2 mg of each) were methylated by the method of Ciucanu and Kerek [Ciucanu, C. and Kerek, F., *Carbohydr. Res.*, 131 (1984) 209–217]. The permethylated heptose derivatives or oligosaccharides were purified on a silica gel column (silica gel 60, 70–230 mesh, 0.5×5 cm). To do this, the columns were equilibrated with chloroform and eluted with an increasing concentration of methanol (M) in chloroform (C) (C-M 95:5; v/v). Trideuterio-labeled permethylated heptose derivatives were produced in an analogous manner by derivatizing with trideuterioiodomethane (CD$_3$I) in place of iodomethane. The heptose was perethylated using ethyl iodide in place of iodomethane.

3.2.3 Reductive cleavage of the dimethylcarbamoyl radical using lithium aluminum hydride Systematic preliminary investigations on the permethylated 7-O-carbamoylheptose revealed that the 7-O-carbamoyl substituent is retained as N,N-dimethyl-7-O-carbamoyl radical on the heptose after dephosphorylation (48% HF), NaOAC hydrolysis, methanolysis and permethylation. To liberate 7-O-carbamoylheptose, 2 mg of each of the permethylated N,N-dimethyl-7-O-carbamoylheptose monomer 3 or dimer 12 were dissolved in dry diethyl ether (1 ml) and stirred with 7.5 mg of lithium aluminum hydride (LiAlH$_4$) at room temperature for 30 min. The solvent was blown off in a stream of nitrogen, and excess LiAlH$_4$ was decomposed by dropwise addition of water. For further purification, the product was taken up in chloroform/methanol (98:2, v/v) and, after removal of the excess salt by centrifugation, was dried (yields: 7, 0.9 mg and 13, 0.7 mg).

3.2.4. Regioselective resubstitution of the decarbamoylated heptose mono- and dimer The heptose derivatives 7 and 13 were heated with N,N-dimethylcarbamoyl chloride (50 µl, SIGMA) in pyridine (500 µl) at 85° C. for 4 h. Subsequently, the solvent and reagent were removed under oil pump vacuum and the product was investigated by mass spectrometry. As an alternative to the resubstitution using N,N-dimethylcarbamoyl chloride, derivatization was carred out with acetic anhydride/pyridine (3.2.1.) and the resulting products (8 and 14) were investigated by GLC-MS.

3.2.5. Methylation analysis of the heptose to determine the binding ratios in the heptose region The methylation analysis was used initially to determine the site of substitution of the carbamoyl radical. To do this, monosaccharide 3, disaccharide 12 and permethylated oligosaccharide were initially hydrolyzed with 0.5 ml of 2M trifluoroacetic acid (TFA, Merck) at 120° C. for 1 h. The N,N-dimethyl-7-O-carbamoyl radical is completely eliminated under these conditions. Excess TFA was stripped off by evaporation with distilled water in a rotary evaporator three times. The sample is subsequently reduced with sodium borodeuteride (NaBD$_4$) and acetylated, and the partially methylated deutero-reduced heptitol acetate is investigated by GC and GC-MS. 3.3. Assignment of the carbamoylheptose to the L-glycero-D-manno-heptitol and D-glycero-D-manno-heptitol configuration All of the heptoses hitherto found in the LPS have, without exception, the L-glycero-D-manno-heptopyranose or D-glycero-D-manno-heptopyranose configuration. In order to be able to assign the 7-O-carbamoylheptose to one of these configurations, 4 mg of the LPS were dephosphorylated to LPS-HF. The 7-O-carbamoyl substituent was subsequently selectively eliminated under mild alkaline conditions (0.5M NaOH, room temperature, 30 min). We showed by kinetic studies that the carbamoyl radical is selectively eliminated under these conditions without involving damage to the heptose. Subsequently, hydrolysis (0.1M HCl, 48 h, 100° C.), reduction (5% NaBH$_4$ in 10 mM NaOH, overnight, room temperature) and peracetylation (Ac$_2$O/pyridine) were carried out. Relative allocation of the configuration took place by means of GC analysis by comparison with the retention times of standard L-glycero-D-manno-heptitol and D-glycero-D-manno-heptitol which can easily be distinguished in the GLC as pairs of diastereomers. GC conditions: column SPB-5® (30 m, 0.25 mm, 0.25µ, Supelco); gradient: 150° C. for 3 min, then 5°/min to 330° C.

3.4. Screening process for determining 7-O-carbamoylheptose in dried bacteria

Dried bacteria (0.2 g) are suspended in 0.5 ml of 48% aqueous HF (Merck) and stirred vigorously at 4° C. in a Teflon vessel equipped with a Teflon stirrer overnight. The retentate from subsequent exhaustive dialysis against distilled water was freeze-dried. The 7-O-carbamoylheptose was then liberated from the LPS in the biomass by methanolysis (0.5M HCl/MeOH, 85° C., 30 min) and methylated [Ciucanu, C. and Kerek, F., *Carbohydr. Res.*, 131, (1984) 209–217] and the permethylated product was removed by centrifugation (3000 rpm, 15 min, Rotixa, Hettlich). The fatty acid methyl esters of lipoid A were subsequently removed using a small column (silica gel 60, 70–230 mesh, 0.5×30 mm, Merck) in 5 ml of ether/n-hexane (40:60), v/v) and then the product (3) was eluted with chloroform/methanol (C-M 95:5, v/v) and analyzed and quantified by GLC-MS on an SPB-5® column. The retention time ($t_R$) of the permethylated methyl-7-O-(N,N-dimethylcarbamoyl)-L-glycero-α-D-manno-heptopyranose anomeric structures (3α and 3β) was 17.76 min and 17.86 min respectively under the stated conditions (SPB-5®).

3.5. Isolation of 7-O-carbamoyl-LαD-Hepp-(1→3)-LαD-Hepp-(1→OMe), 9α, for NMR analysis To isolate and prepare pure disaccharides 9α, initially 50 mg of LPS were hydrolyzed (0.1M HCl, 100° C., 85 min) and the precipitated lipoid A was removed by centrifugation. The supernatant was further purified on Sephadex G-10 (2.5×120 cm, water) and subsequently lyophilized. This core oligosaccharide was suspended in 4×0.5 ml aliquots in aqueous HF (48%, Merck) and vigorously stirred in Teflon vessels overnight. Drying at the oil pump (6 h) was followed by hydrolysis (0.5M HCl/MeOH, 85° C., 30 min) and the amino-containing components GalN and Ala were removed from the hydrolyzate on an ion exchanger (Amberlite IR-120, H$^+$ form). After the exchanger resin had been washed (50 ml), the H$_2$O eluate was further purified by HPLC. The purified disaccharide 9α, which was found at R$_f$=0.54 in TLC, eluted in the HPLC with a retention time of 21 min (yield of 9α, 1.23 mg).

3.6. Isolation of LαD-Hepp-(1→3)-LαD-Hepp-(1→OMe), 10α, and LαD-Hepp-(1→OMe), 2α, from the synthetic disaccharide LαD-Hepp-(1→3)-LαD-Hepp as reference substances for the NMR analysis 3.8 mg of the synthesized disaccharide 3-O(L-glycero-α-D-manno-heptopyranosyl)-L-glycero-D-manno-heptopyranose [Paulsen, H. et al., Liebigs. Ann. Chem., (1986), 675–686) were incubated in 0.5M HCl/MeOH at 37° C. overnight. TLC analysis [silica gel 60, chloroform/methanol/water (C-M-W) 100:100:30] revealed that, under these conditions, besides the target structure methyl-3-O-(7-O-carbamoyl-L-glycero-α-D-manno-heptopyranosyl)-L-glycero-α-D-manno-heptopyranose disaccharide (10α) (R$_f$ 0.40), there had also been partial formation of the monosaccharides methyl L-glycero-α-D-manno-heptopyranoside 2α (R$_f$ 0.58) and methyl L-glycero-β-D-manno-heptopyranoside 2β (R$_f$ 0.52). It was possible to separate these individual components in a subsequent HPLC run (Zorbax NH$_2$, 9 250 cm, DuPont) with an increasing gradient from eluent A [CH$_3$CN—H$_2$O 92:8 (v/v)] and eluent B [CH$_3$CN—H$_2$O 50:50 (v/v)] at a flow rate of 3.5 ml/min. It was possible in this case to separate the disaccharide target structure 10α from the monosaccharides 2α and 2β, with the α-anomeric methyl glycosides showing a positive, and the β-anomeric methylheptose showing a negative, signal in the chiral detector. Aliquots of these peaks were tested once again by TLC (C-M-W 100:100:30). The purified disaccharide 9α (TLC R$_f$=0.4) eluted in the HPLC with a retention time of 99 min, 2α (40 min, TLC R$_f$ 0.58) and 2β (54 min, TLC R$_f$ 0.52). The yields were: 10α, 0.81 mg, 2α 1.7 mg, 2β 0.70 mg.

4. Results and discussion

To characterize the heptose required according to the invention, firstly the nature and position of the carbamoyl radical on the heptose were determined by means of various labeling experiments in the GC-MS analysis. Then the linkage of the two heptoses found in the core oligosaccharide of *Pseudomonas aeruginosa* PAC605 LPS and the substitution pattern of the carbamoyl radical in the disaccharide were likewise determined by GC-MS. Finally, the heptose disaccharide was isolated with the 7-O-carbamoyl radical on the heptose in intact form and underwent detailed analysis by one- and two-dimensional NMR spectrometry with $^1$H- and $^{13}$C-homo- ($^1$H,$^1$H-COSY) and heteronuclear ($^1$H,$^{13}$C-COSY) correlation. After the 7-O-carbamoyl-L-glycero-D-manno-heptopyranose had been identified, a screening process for determination thereof in bacteria was developed without previous extraction of the LPS.

4.1. GC-MS analysis of the 7-O-carbamoylheptose as per-O-acetylated derivative 5

Figure 1B:
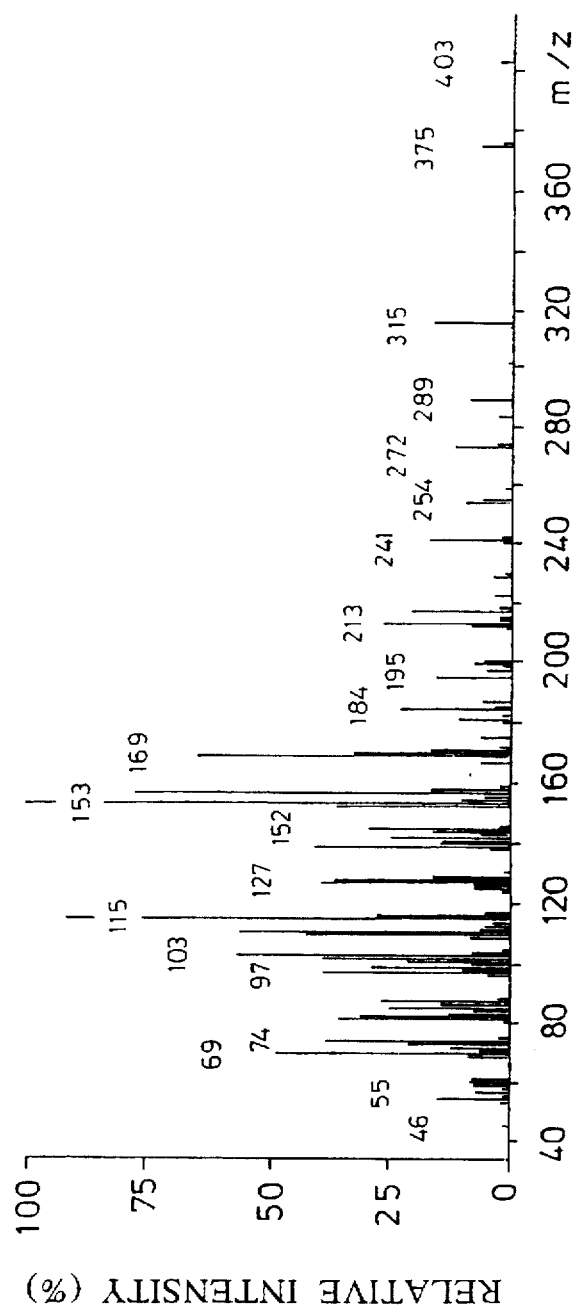
Figure 1C:
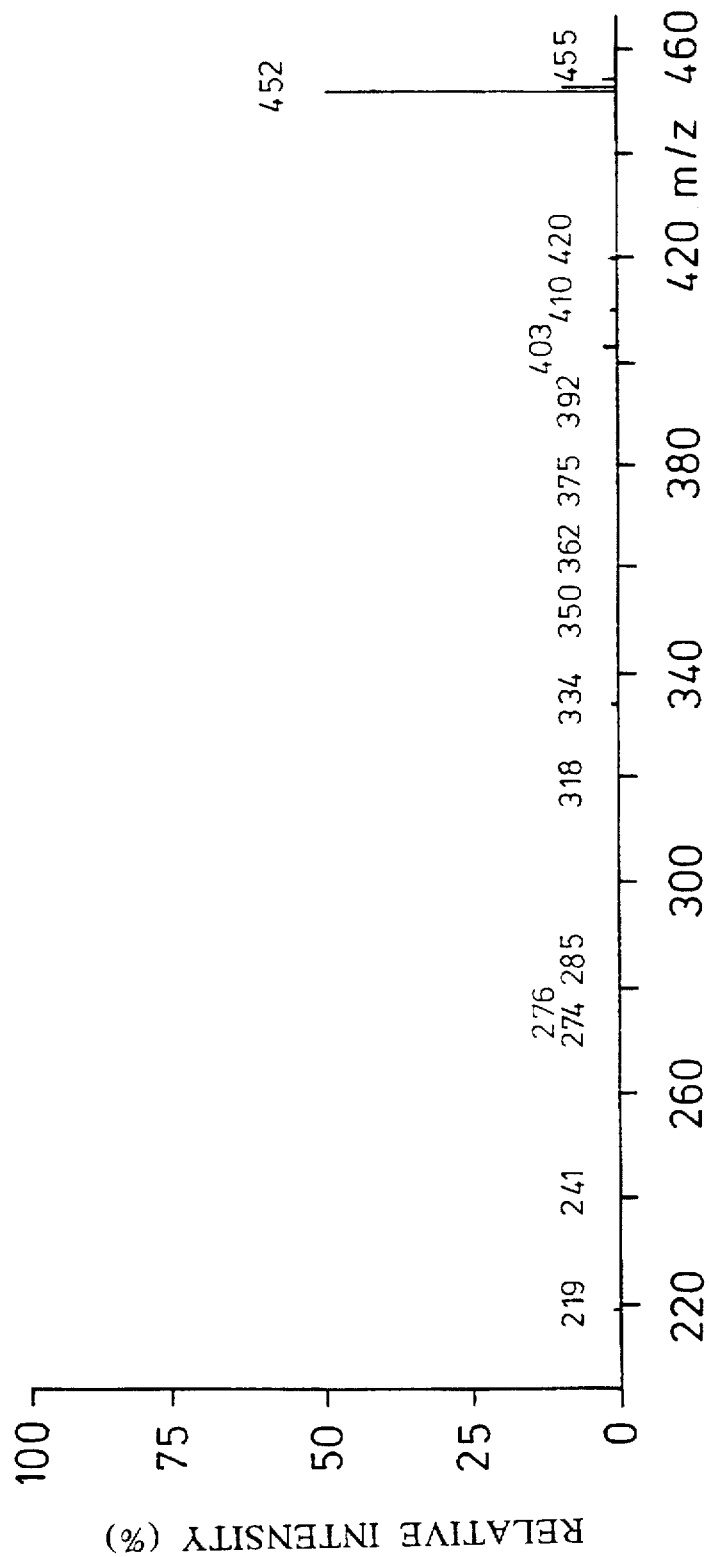
Figure 2A:
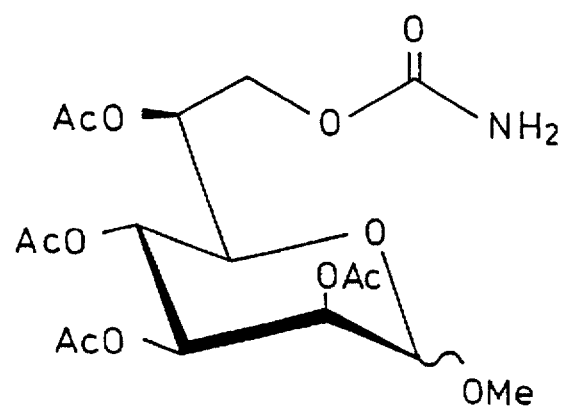
FIG. 2 shows the structural formula, the electron impact mass spectrum (1) and the Cl—|NH$_3$| mass spectrum (2) of methyl-2,3,4,6,7-tetra-O-acetyl-7-O-carbamoyl-D-glycero-α/β-D-manno-heptopyranose (compound No. 5).
Figure 2B:
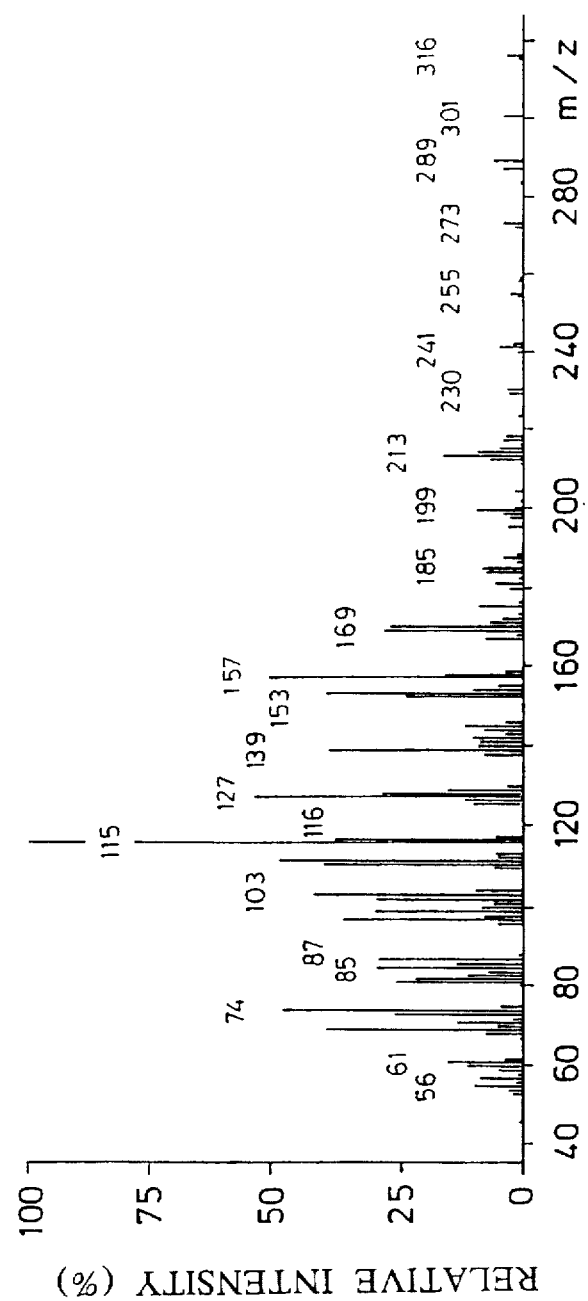
Figure 2C:
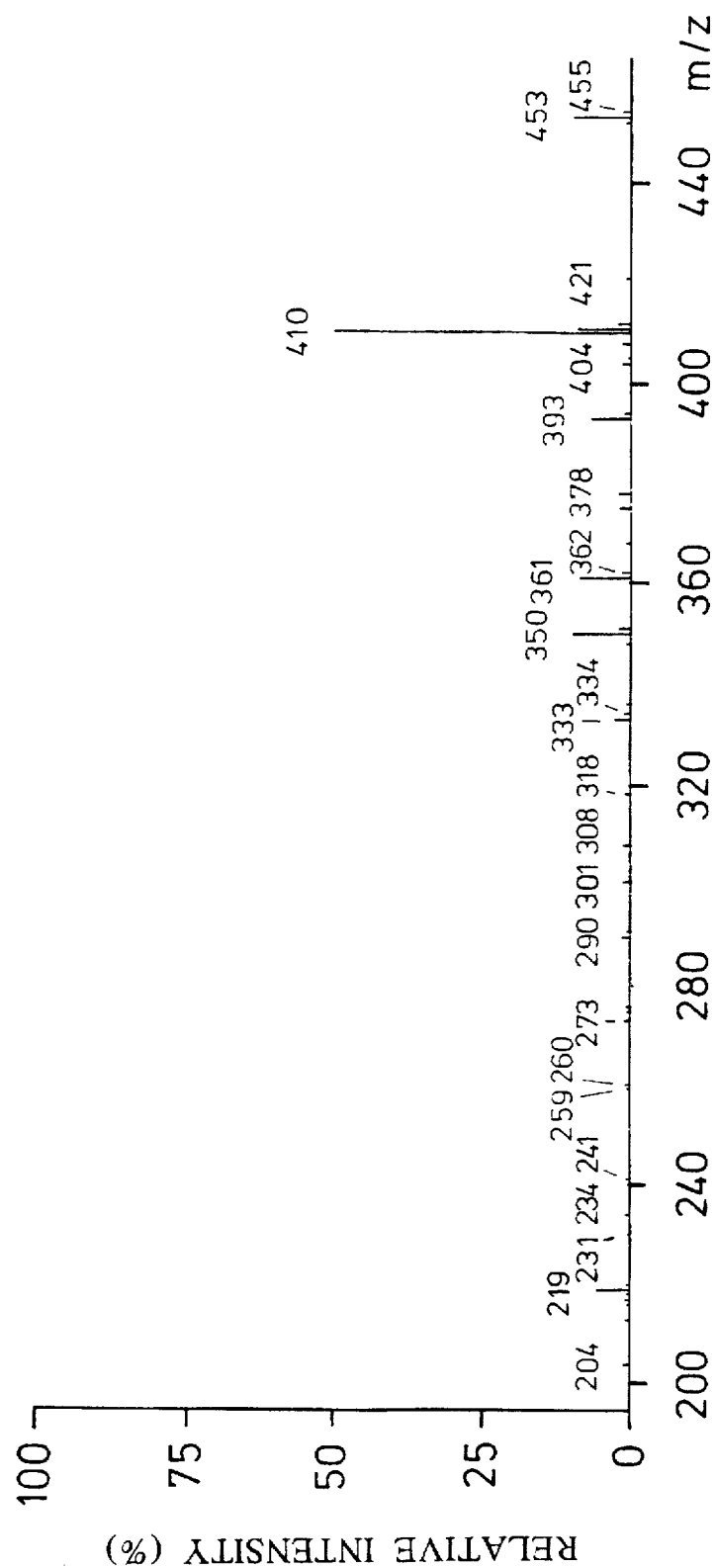

Methanolysis (85° C., 2M HCl/MeOH, 30 min) of isolated, dephosphorylated core oligosaccharide from *P. aeruginosa* PAC605 LPS, per-O-acetylation and subsequent GC-MS analysis showed two different heptoses. One eluted as methyl 2,3,4,6,7-penta-O-acetylheptopyranoside (4) with a shorter retention time (t$_R$=17.4 min) than a second, preivously unknown heptose derivative (t$_R$=21.5 min). In the CI-MS, both heptoses showed a pseudo-molecular ion peak [M+NH$_4$]$^+$=452 (4) and [M+NH$_4$]$^+$=453 (5) (FIGS. 1 and 2). The difference in mass of one atomic mass unit (AMU) between 4 and 5, and the significantly increased retention time can be explained by the replacement of an acetyl radical (CO—CH$_3$) in 4 by a carbamoyl radical (CO—NH$_2$) in 5.

4.2. Identification of the carbamoyl group by GC-MS

To identify the carbamoyl group and determine its site of substitution, variously labeled derivatives of the unknown heptose were produced for the GC-MS analysis (3–8) in order to be able to prove the structure with this method.

Figure 3A:
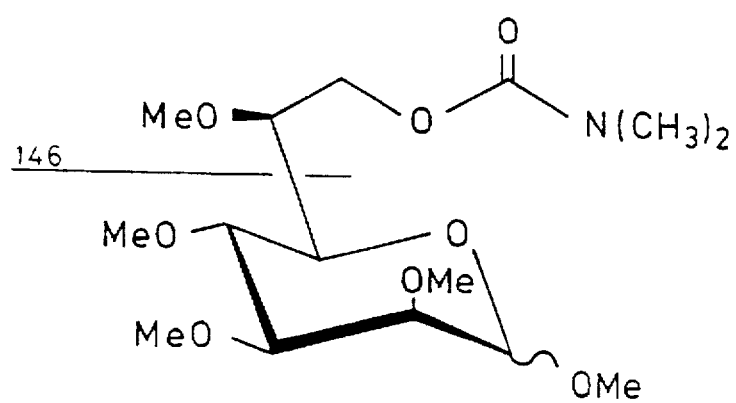
FIG. 3 shows the structural formula, the electron impact mass spectrum (1) and the Cl—|NH$_3$| mass spectrum (2) of methyl-7-O-(N,N-dimethylcarbamoyl)-2,3,4,6-tetra-O-methyl-D-glycero-α/β-D-manno-heptopyranose (compound No. 3).
Figure 3B:
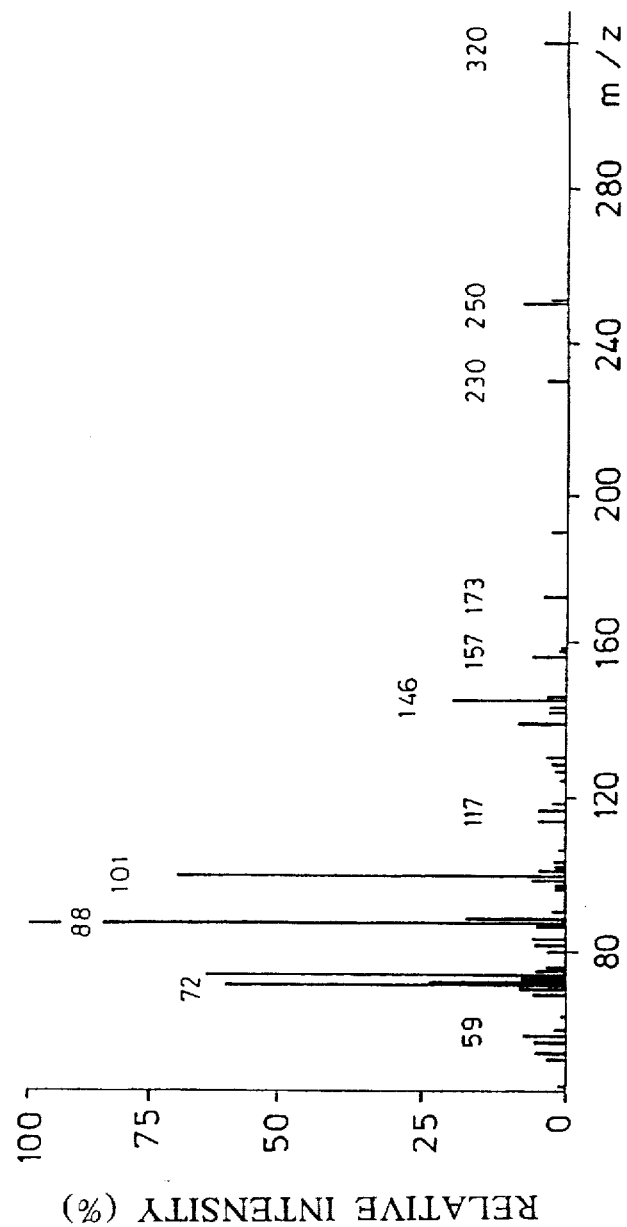
Figure 3C:
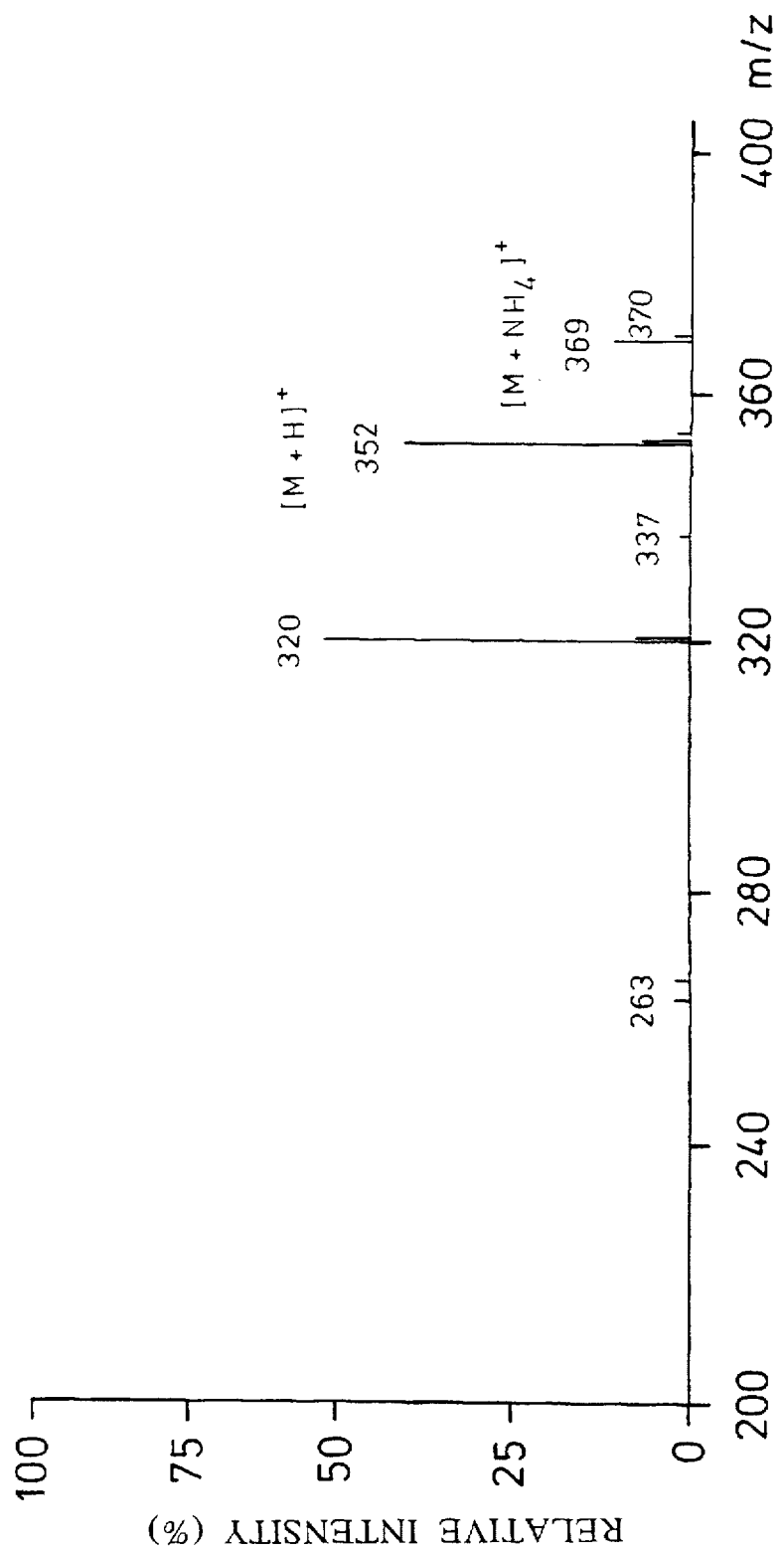
Figure 4A:
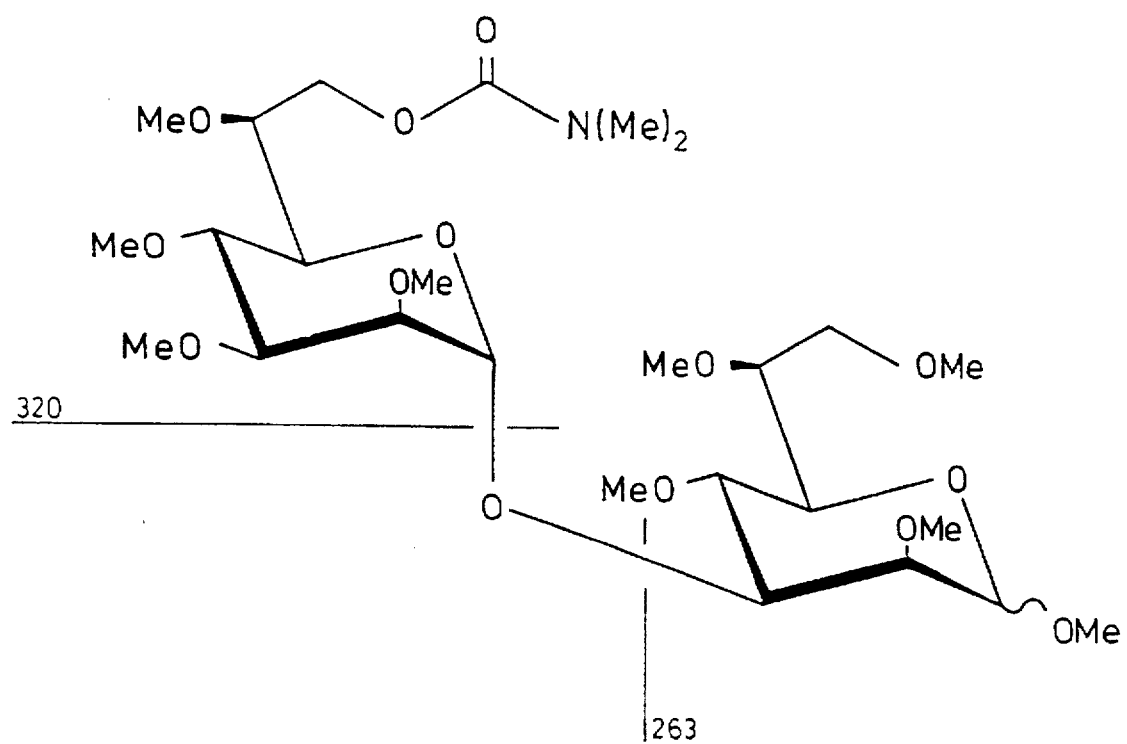
FIG. 4 shows the structural formula, the electron impact mass spectrum (1) and the Cl—[NH$_3$] mass spectrum (2) of methyl 3-O-[7-O-(N,N-dimethylcarbamoyl)-2,3,4,6-tetra-O-methyl-heptopyranosyl]-2,4,6,7-tetra-O-methyl-heptopyranoside (compound No. 12).
Figure 4B:
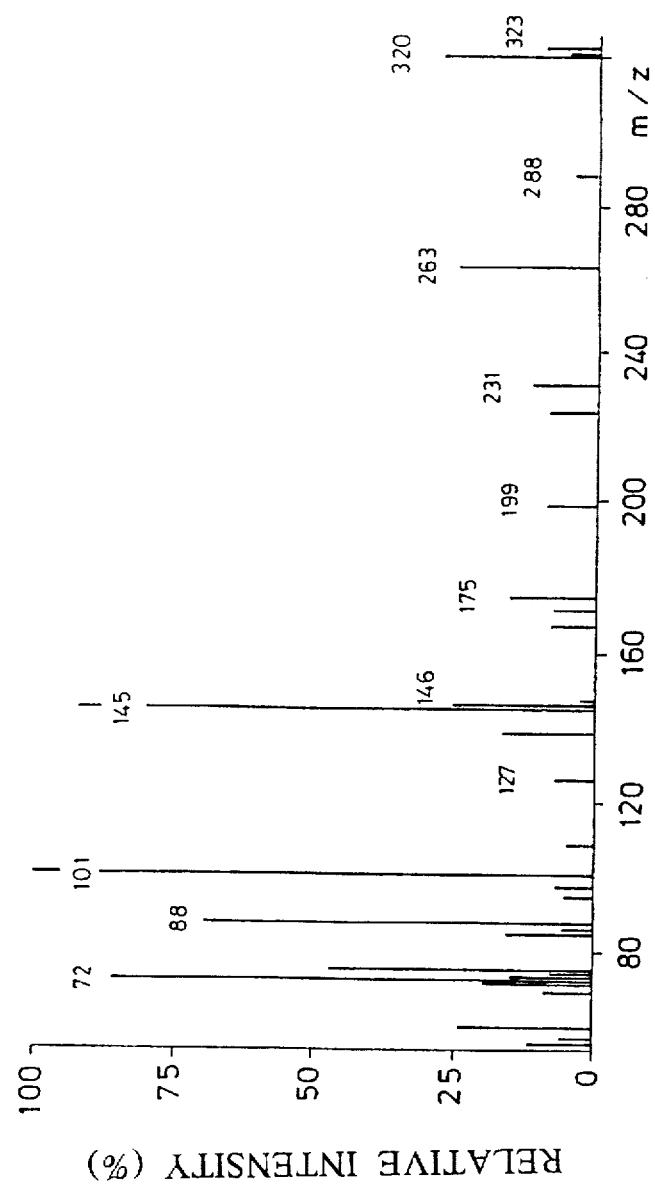
Figure 4C:
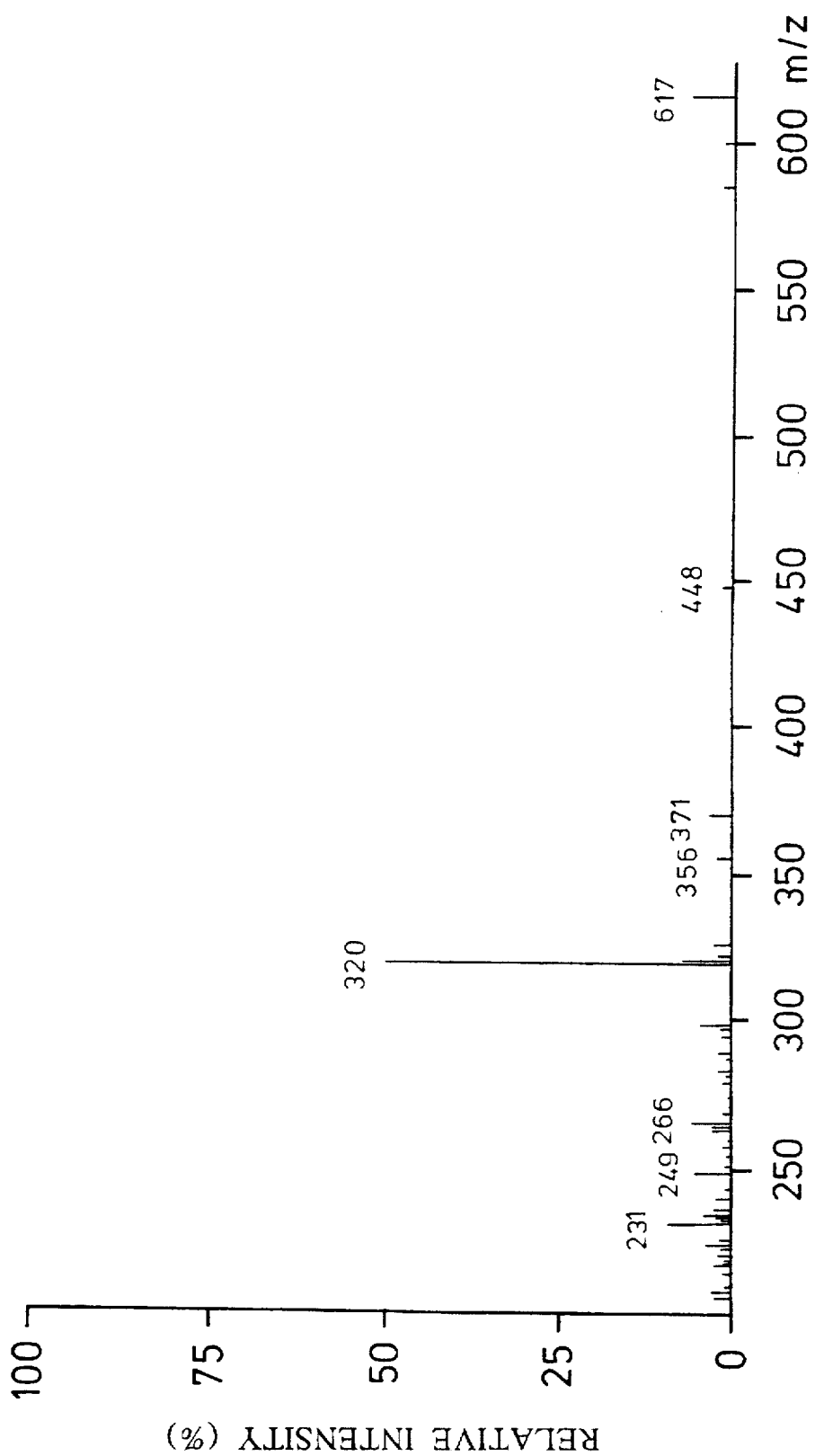

4.2.1. GC-MS analysis of the permethylated 7-O-carbamoylheptose as mono- and disaccharide After dephosphorylation and methanolysis, the methyl glycosides of the heptose were permethylated. It was possible in this case to identify the permethylated 7O-carbamoylheptose both as methyl 7-O-(N,N-dimethylcarbamoyl)-2,3,4,6-tetra-O-methylheptopyranoside (3) and as methyl 3-O-[7-O-(N,N-dimethylcarbamoyl)-2,3,4,6-tetra-O-methylheptopyranosyl]-2,4,6,7-tetra-O-methylheptopyranoside (12) in the GC-MS analysis (FIG. 3 and FIG. 4). Moreover the monosaccharide 3 showed in the EI-MS a characteristic fragment ion with m/z=320 [M—OCH$_3$]$^+$ and m/z=146 which can be explained by the mass fragment [HC=O$^+$Me—CO—N(CH$_3$)$_2$] which derives from cleavage of the C-5/C-6 bond. This made it probable in the first place that the carbamoyl radical was a substituent on C-6 or C-7.

The disaccharide 12 (t$_R$=34.3 min) (FIG. 4) showed in the EI-MS a mass fragment with m/z=320, which indicated that the carbamoyl substituent must have been located on the second, nonreducing heptose (Hep II). This interpretation is consistent with the existence of a mass fragment with m/z=263, which was assigned to the permethylated, reducing heptopyranose (Hep I). The results of the CI-MS support this interpretation ([M+NH$_4$]$^+$=617, FIG. 4). It was possibly by perethylation in place of permethylation to convert monosaccharide 3 and disaccharide 12 into the relevant perethylated derivatives, it being possible to introduce 6 and 10, respectively, ethyl groups in place of the methyl group into 3 and 12, which was detectable in the MS analysis by a mass increment of Δm/z=14 AMU per ethyl radical introduced (detailed spectra not given here).

Figure 5A:
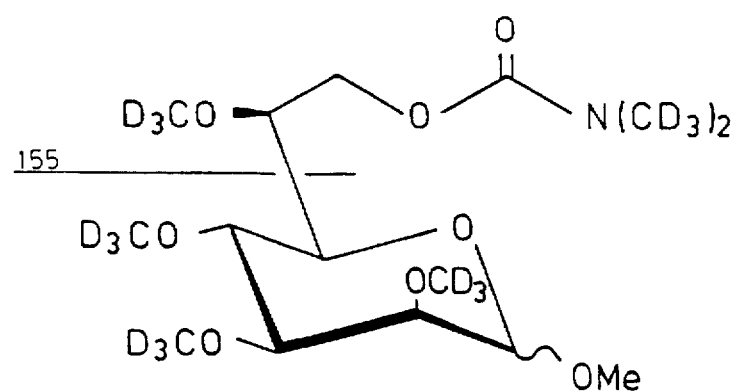
FIG. 5 shows the structural formula and the electron impact mass spectrum of methyl-7-O-[N,N-di-(trideuteriomethyl)-carbamoyl)-2,3,4,6-tetra-O-trideuteriomethyl-D-glycero-α/β-D-manno-heptopyranose (compound No. 6).
Figure 5B:
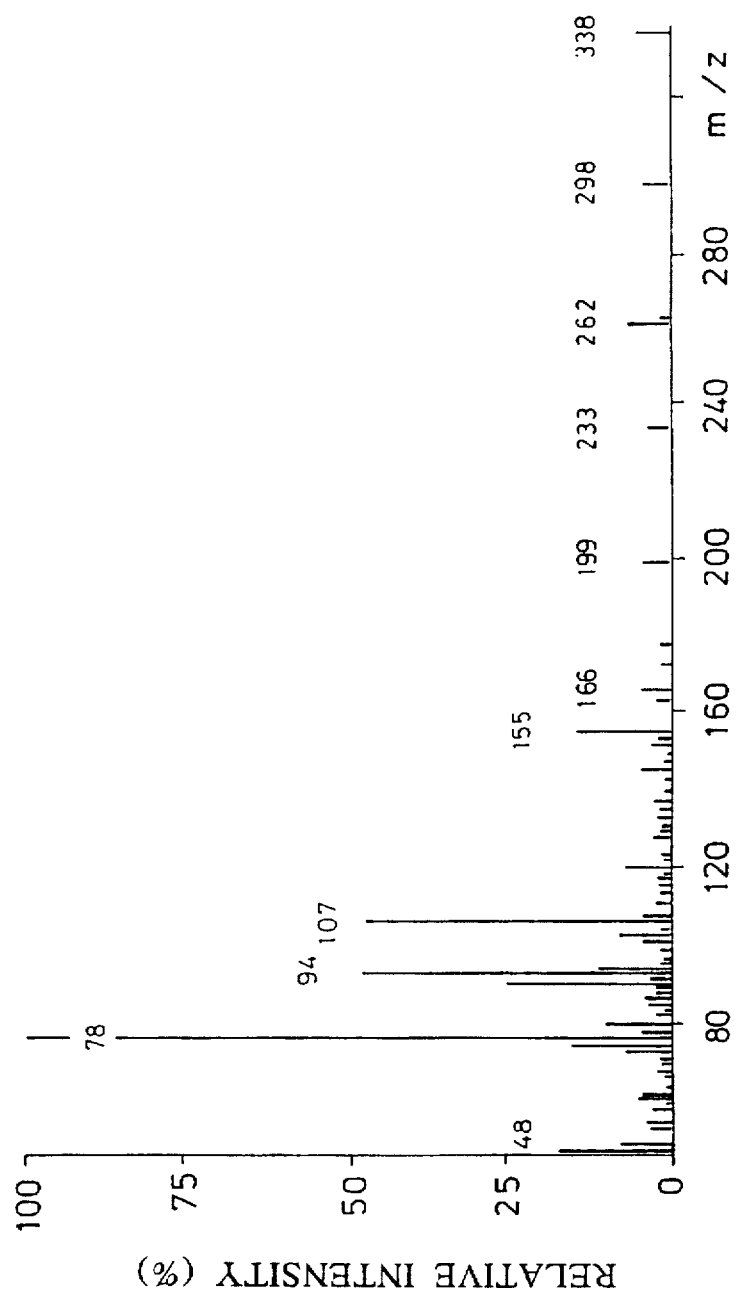

4.2.2. Labeling experiments and GC-MS analysis on 7-O-carbamoylheptose mono- and disaccharide Methylation with iodomethane-d$_1$ in place of iodomethane allowed compound 6 to be identified as monosaccharide in the GC-MS analysis (FIG. 5). Once again, the characteristic [M—OMe]$^+$ fragment with m/z=338 was observed, which corresponds to the fragment with m/z=320 in 3·m/z=155 was found analogously and was derived from cleavage of the C-5/C-6 bond. It was thus possible unambiguously to locate the carbamoyl group in position C-7 of the heptose from the fragment with m/z=107 |CH=O—CO—N(CD$_3$)$_2$| which corresponds to the nondiagnostic m/z=101 |CH=O—CO—N(CH$_3$)$_2$| in 3.

4.2.3. Reductive cleavage of the 7-O-carbamoyl radical using LiAlH$_4$

Compounds 7 and 13 were obtained by a mild and selective elimination of the permethylated carbamoyl radical from 3 and 12 respectively using LiAlH$_4$ in ether, and these have a free primary hydroxyl group in position 7 or 7' in place of the permethylated 7-O-carbamoyl group. Regioselective resubstitution of these free hydroxyl groups using N,N-dimethylcarbamoyl chloride in pyridine afforded the starting compounds 3 and 12 which did not differ in respect of retention time and mass fragmentation (EI-MS, CI-MS) from the initial substances. This provided a further indication of the postulated structure.

Figure 6A:
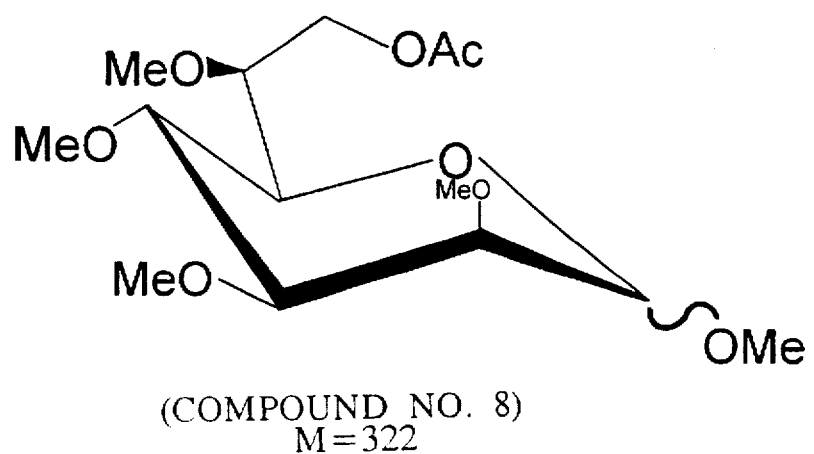
FIG. 6 shows the structural formula, the electron impact mass spectrum (1) and the Cl—[NH$_3$] mass spectrum (2) of methyl-7-O-acetyl-2,3,4,6-tetra-O-methyl-D-glycero-α/β-D-manno-heptopyranose (compound No. 8).
Figure 6B:
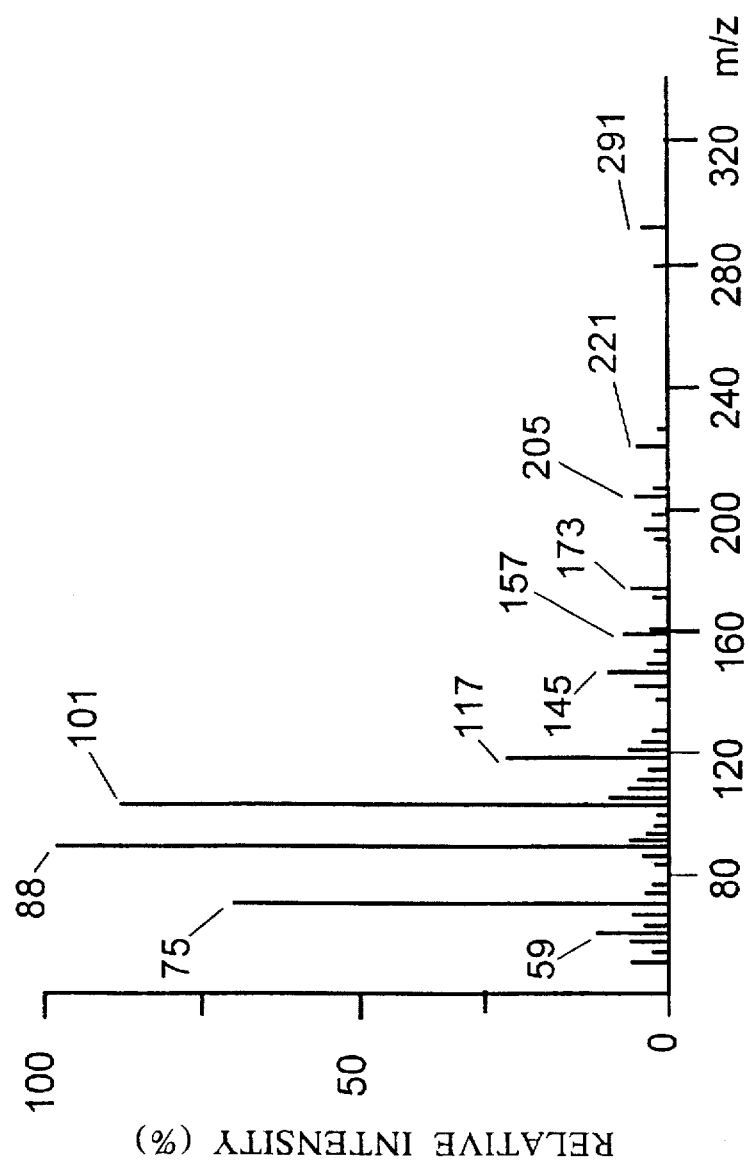
Figure 6C:
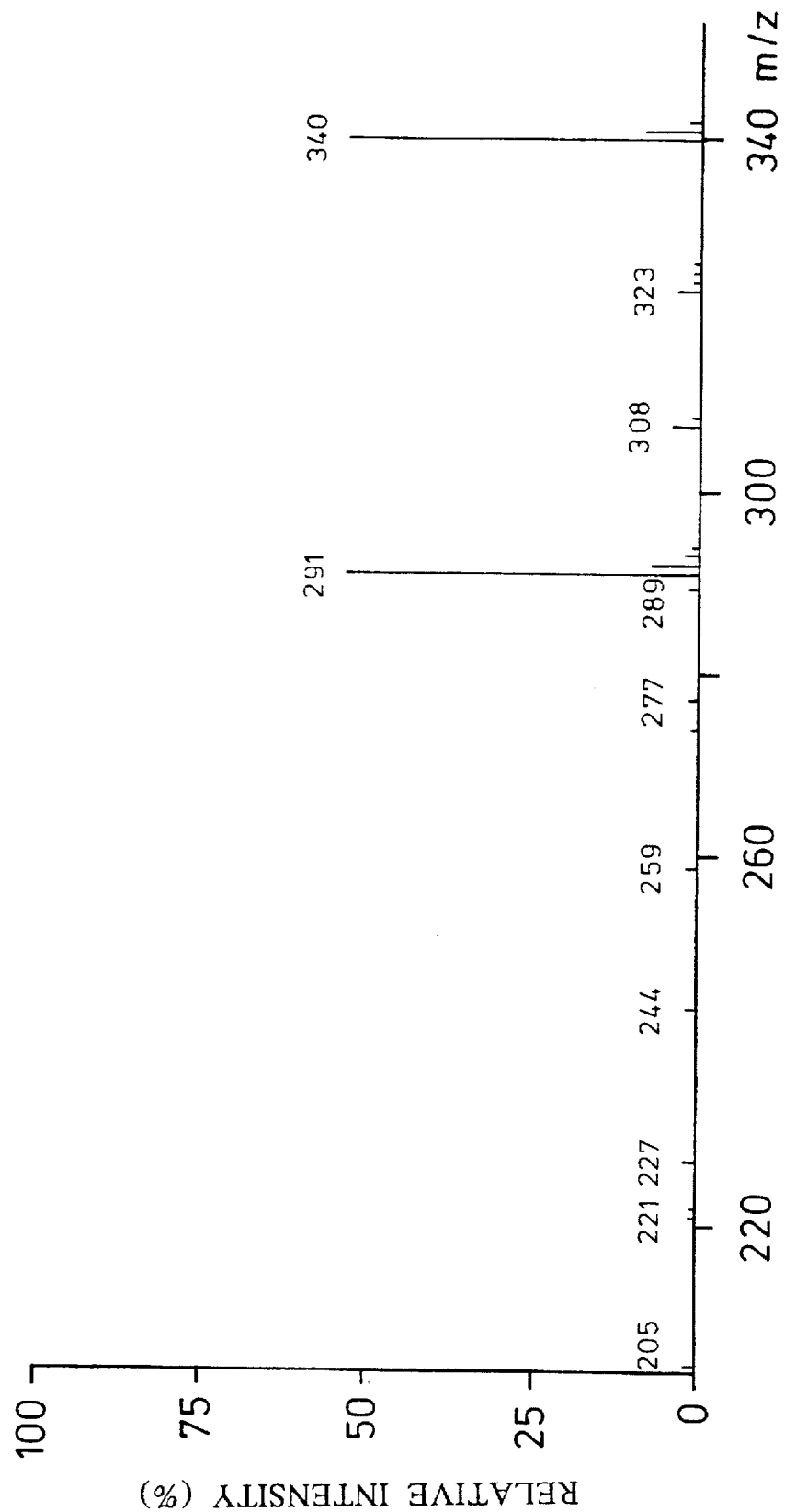
Figure 7A:
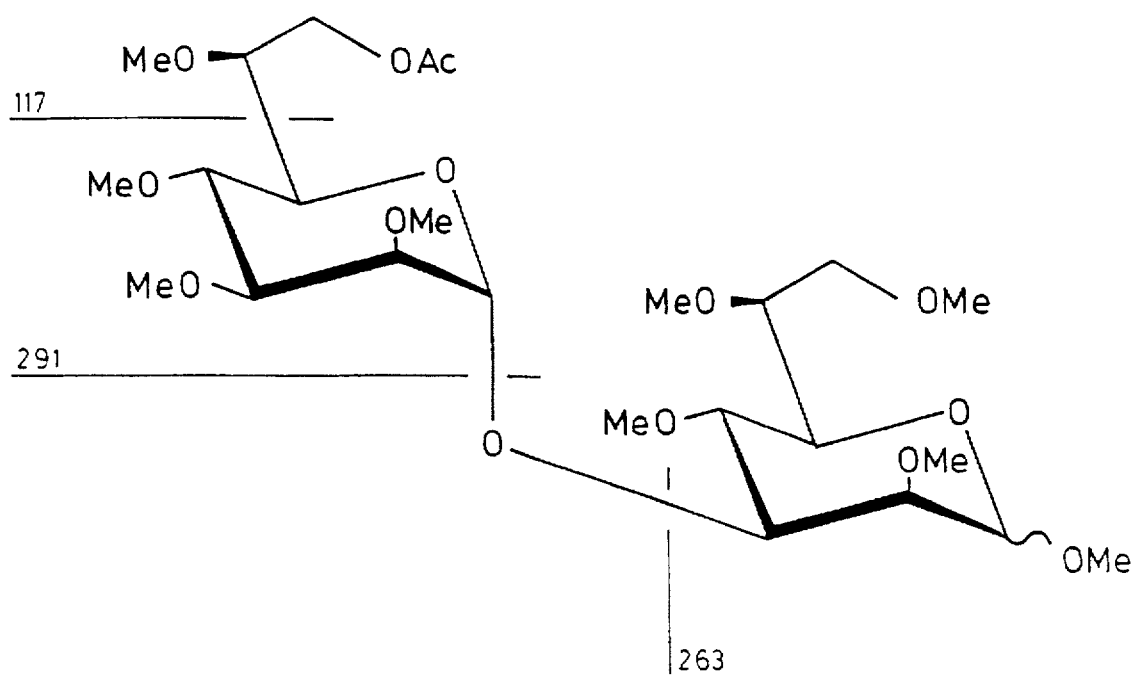
FIG. 7 shows the structural formula, the electron impact mass spectrum (1) and the Cl—[NH$_3$] mass spectrum (2) of methyl 3-O-acetyl-2,3,4,6-tetra-O-methyl-heptopyranosyl]-2,4,6,7-tetra-O-methyl-heptopyranoside (compound No. 14).
Figure 7B:
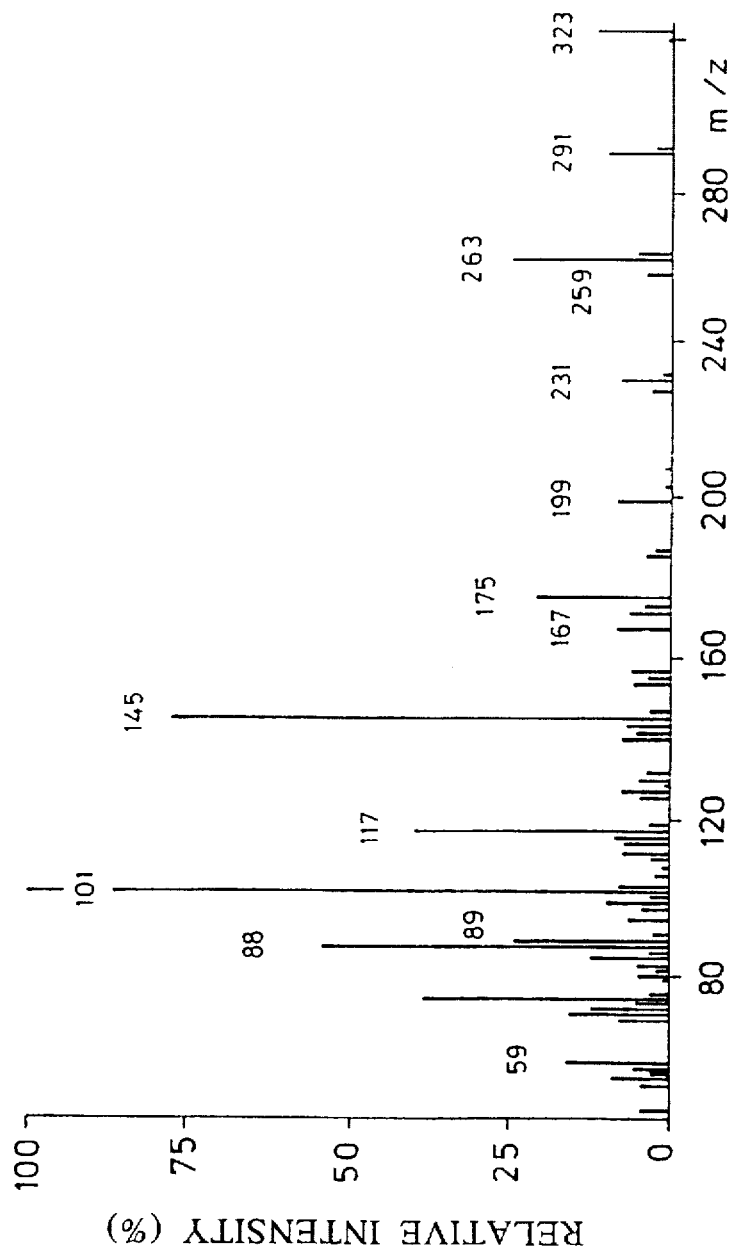
Figure 7C:
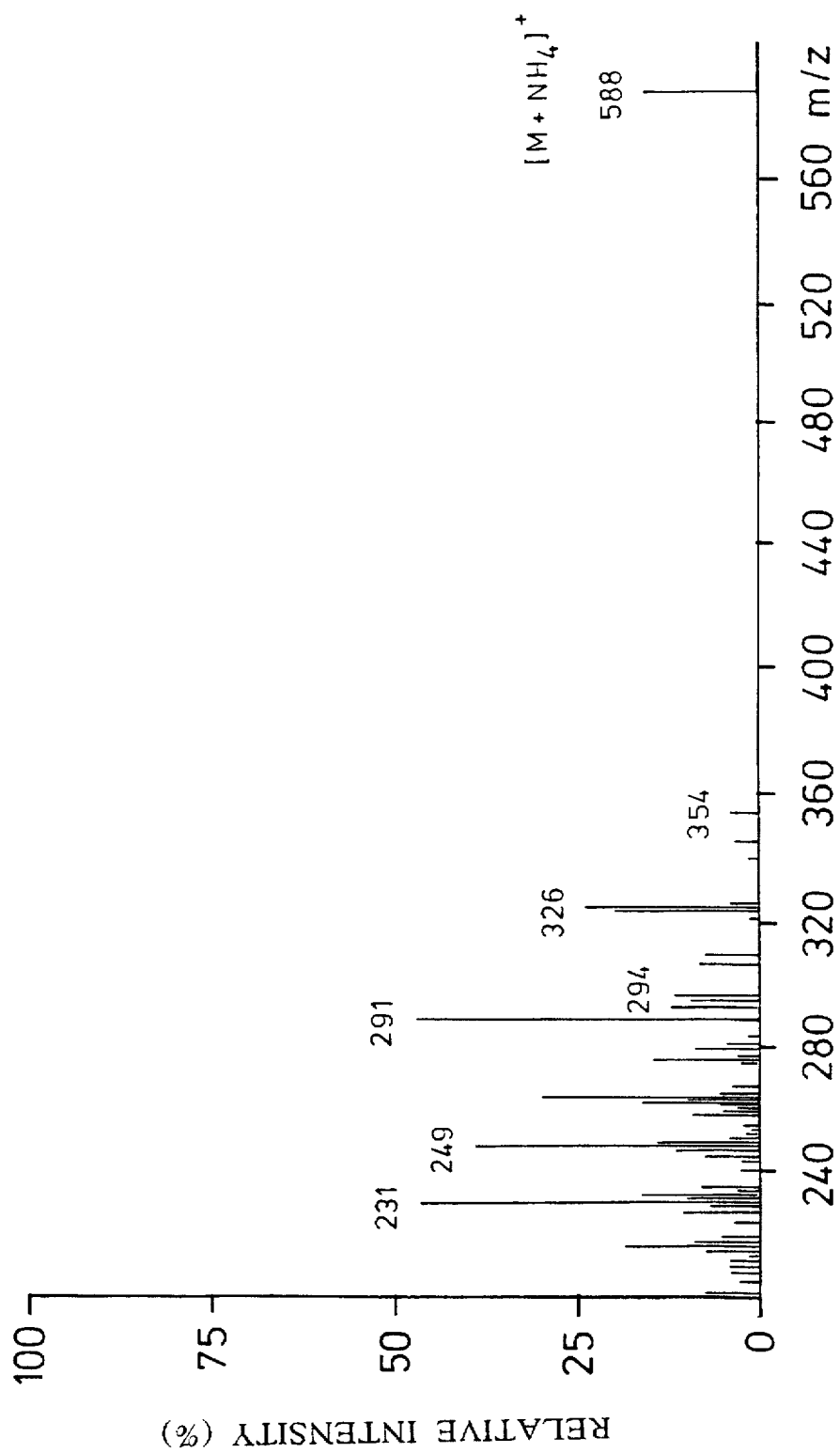

O-acetylation of 7 and 13 results in 8 and 14 respectively (FIG. 6 and FIG. 7), both of which show the charactertistic fragment with m/z=117 [CHOMe—CH$_2$—OAc]$^+$ which is derived from cleavage of the C-5/C-6 bond in the heptose. It was likewise possible to conclude from the fact that the mass fragment with m/z=263 was not changed either in the disaccharide 12 or in 14 that only the terminal heptose (Hep II) was substituted by the carbamoyl radical and that substitution on Hep I is precluded.

4.3. Methylation analysis of the heptose region in the core oligosaccharide

Figure 8A:
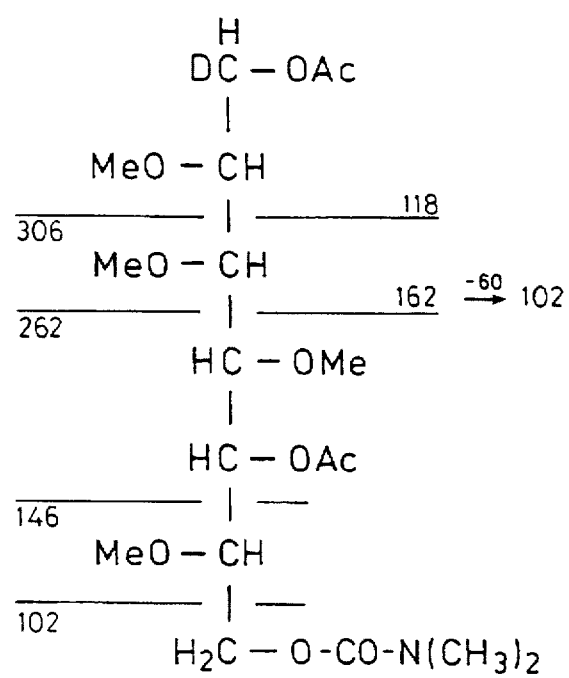
FIG. 8 shows the structural formula, the electron impact mass spectrum (1) and the Cl—[NH$_3$] mass spectrum (2) of 1,5-di-O-acetyl-7-O-(N,N-dimethylcarbamoyl)-2,3,4,6-tetra-O-methyl-heptitol (compound No. 16).
Figure 8B:
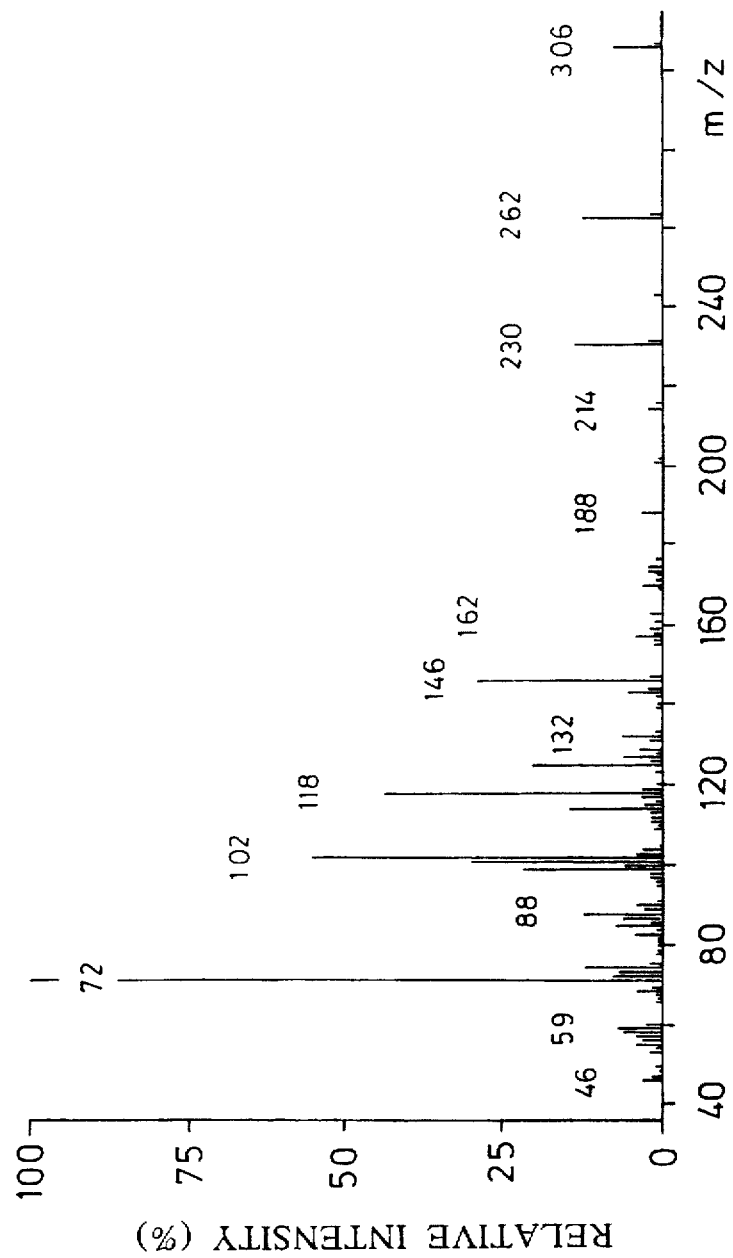
Figure 8C:
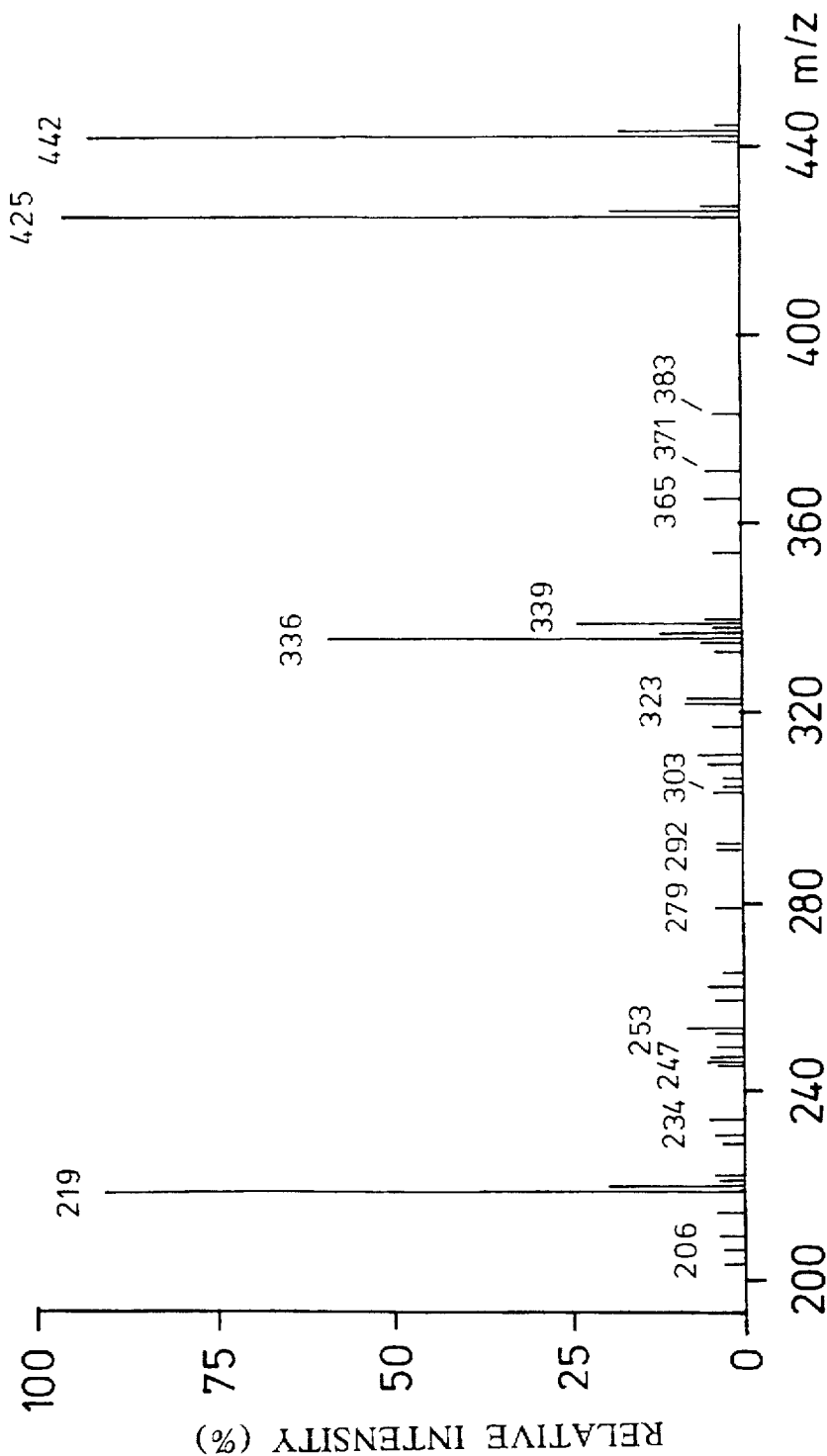
Figure 9A:
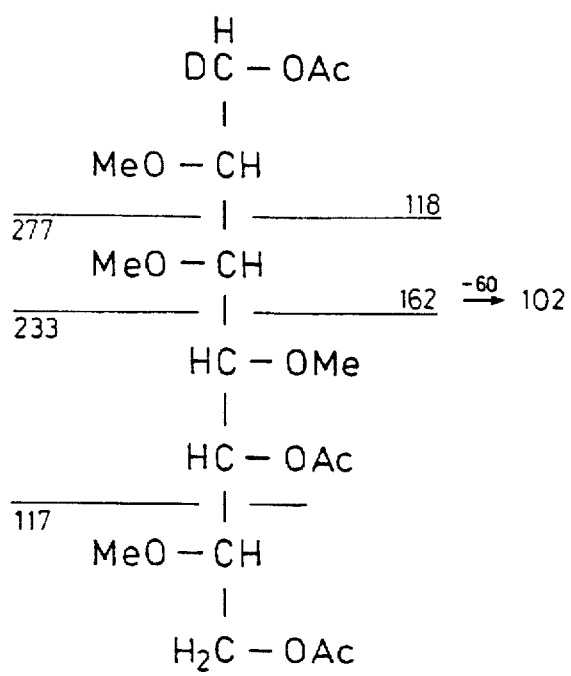
FIG. 9 shows the structural formula and the electron impact mass spectrum of 1,5-tri-O-acetyl-2,3,4,6-tetra-O-methyl-heptitol (compound No. 15).
Figure 9B:
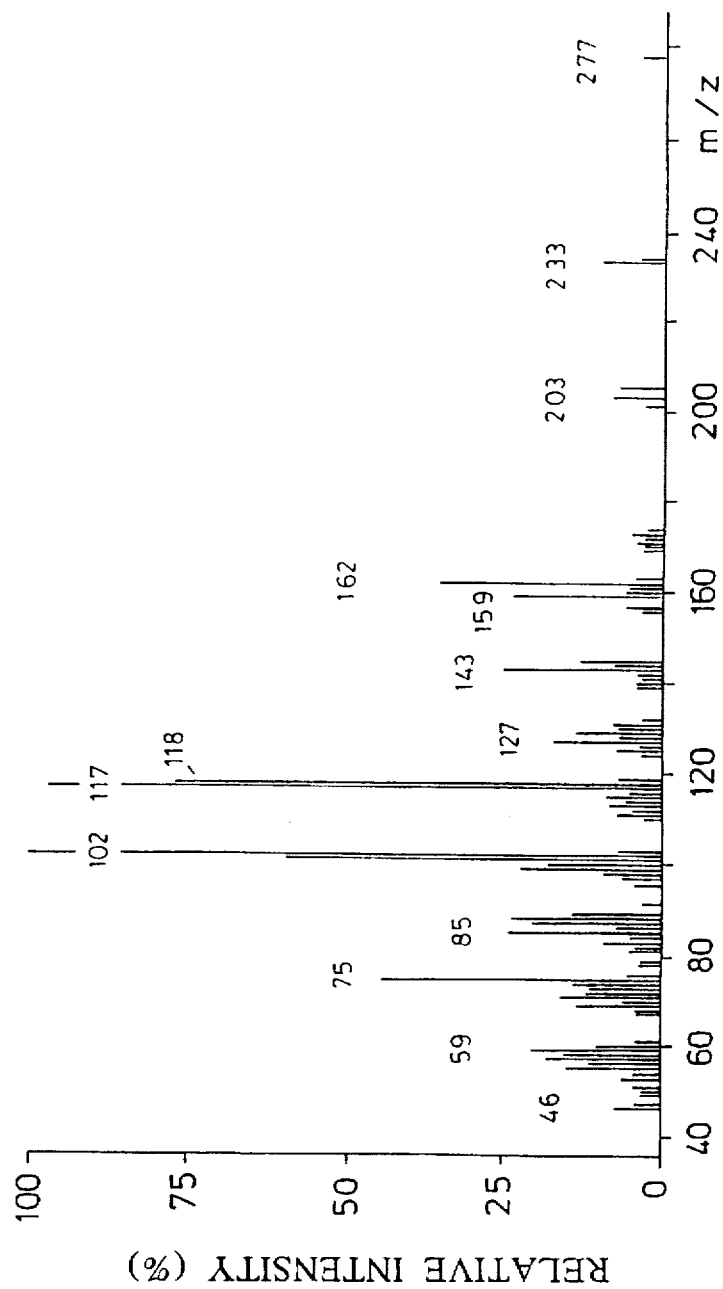

Monosaccharide 3 (3.5 mg) was hydrolyzed (2M TFA, 1 h, 120° C.), reduced (NaBD$_4$) and per-O-acetylated. We found that under these conditions the 7-O-carbamoyl radical is not quantitatively eliminated, and both 1,5,7-tri-O-acetyl-2,3,4,6-tetra-O-methylheptitol 15 (FIG. 9) and 1,5-di-O-acetyl-7-O-[N,N-dimethylcarbamoyl]-2,3,4,6-tetra-O-methylheptitol 16 are obtained (FIG. 8). The partially methylated heptitol acetate 15 (t$_R$=15.1 min, FIG. 9) showed in the CI-MS [M+NH$_4$]$^+$ m/z=413 and [M+H]$^+$ m/z=396 and in the EI-MS fragments with m/z=102 (162–60), 118 and 162 from deuterium-reduced end, and with m/z=117, 223 and 277 from the unreduced end. The partially methylated heptitol 16 (t$_R$=19.7 min) showed in the CI-MS (FIG. 8) [M+NH$_4$]$^+$ m/z=442 and [M+H]$^+$m/z=425 and in the EI-MS fragments with m/z=102 (162–60), 118, 162 from the deuterium-reduced end, and with m/z=102, 146, 262, 306 from the unreduced end. These mass fragments from the partially methylated heptitol acetates provided a further indication of 7-substitution by the carbamoyl radical.

Figure 10A:
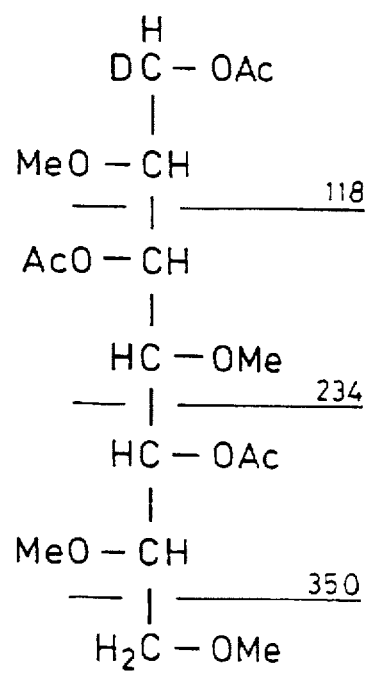
FIG. 10 shows the structural formula, the electron impact mass spectrum (1) and the Cl—[NH$_3$] mass spectrum (2) of 1,3,5-tri-O-acetyl-2,4,6,7-tetra-O-methyl-heptitol (compound No. 18).
Figure 10B:
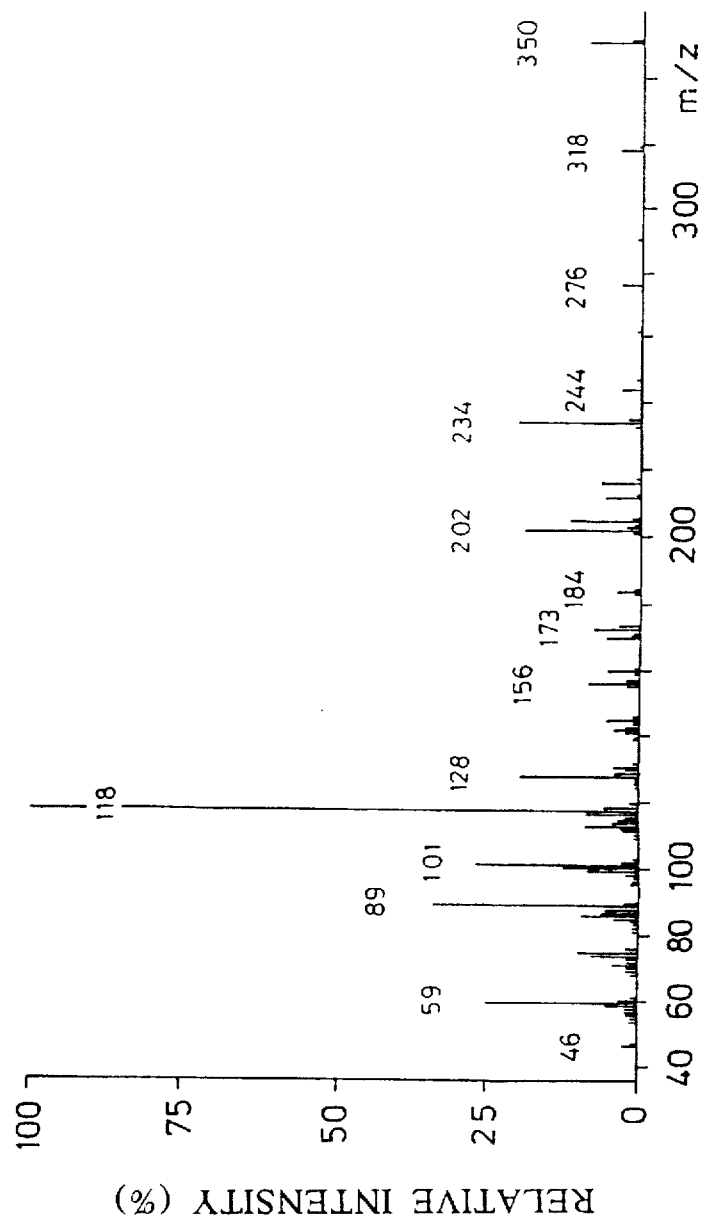
Figure 10C:
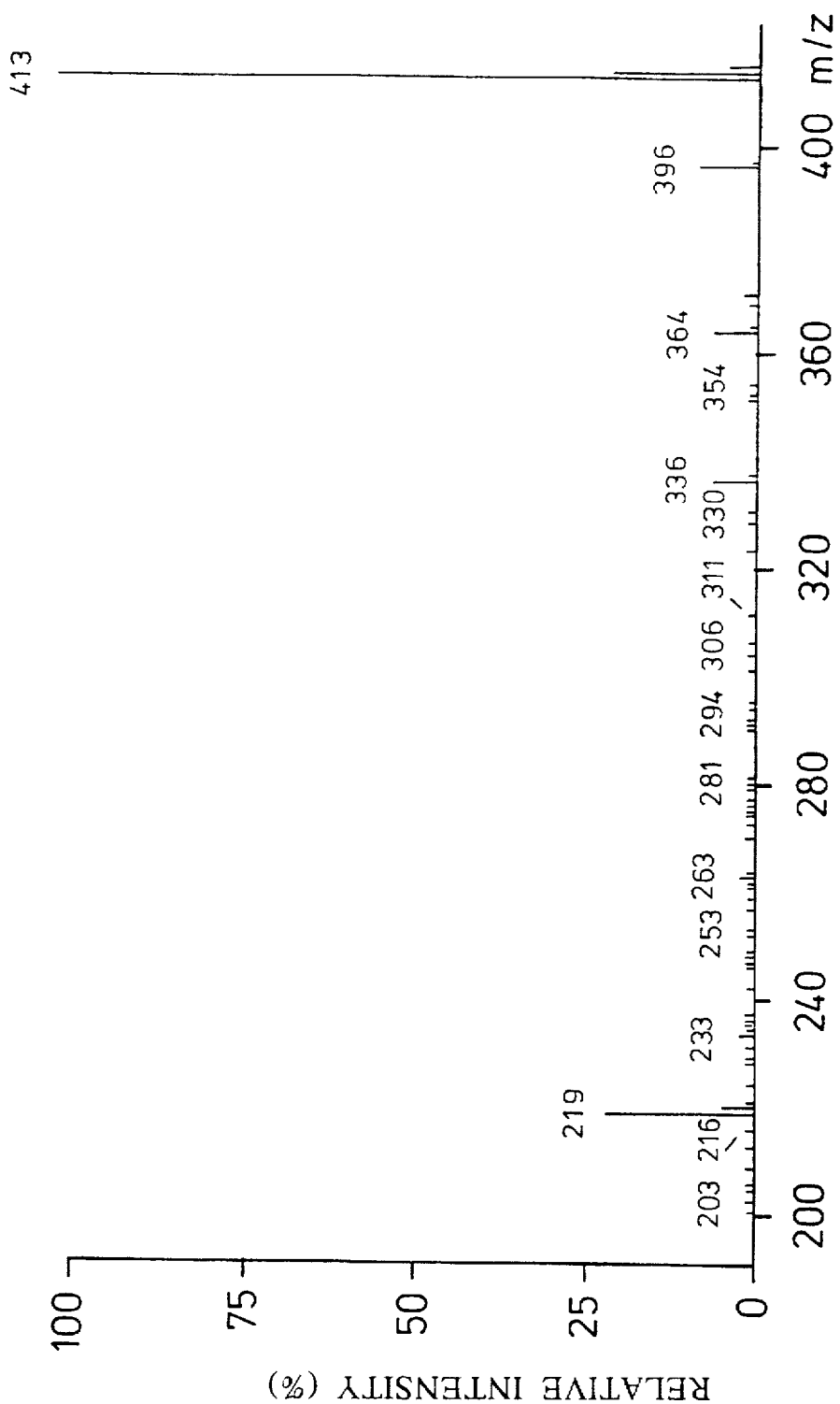
Figure 11A:
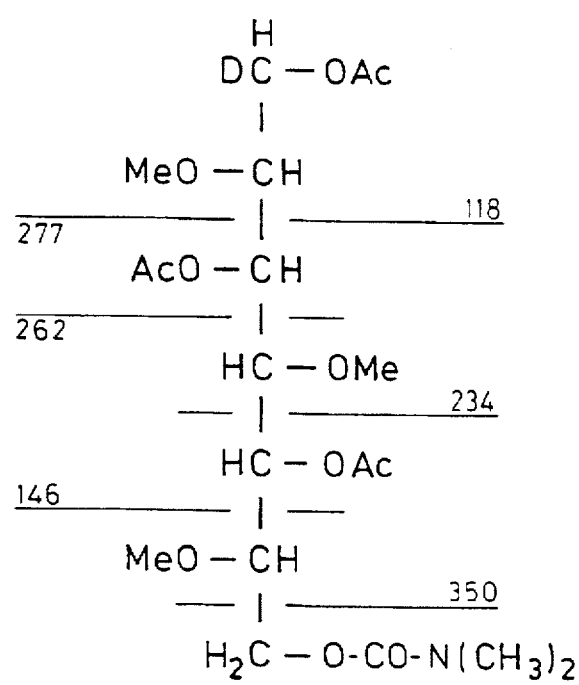
FIG. 11 shows the structural formula and the electron impact mass spectrum of 1,3,5-tri-O-acetyl-7-O-(N,N-dimethylcarbamoyl)2,4,6-tri-O-methyl-heptitol (compound No. 17).
Figure 11B:
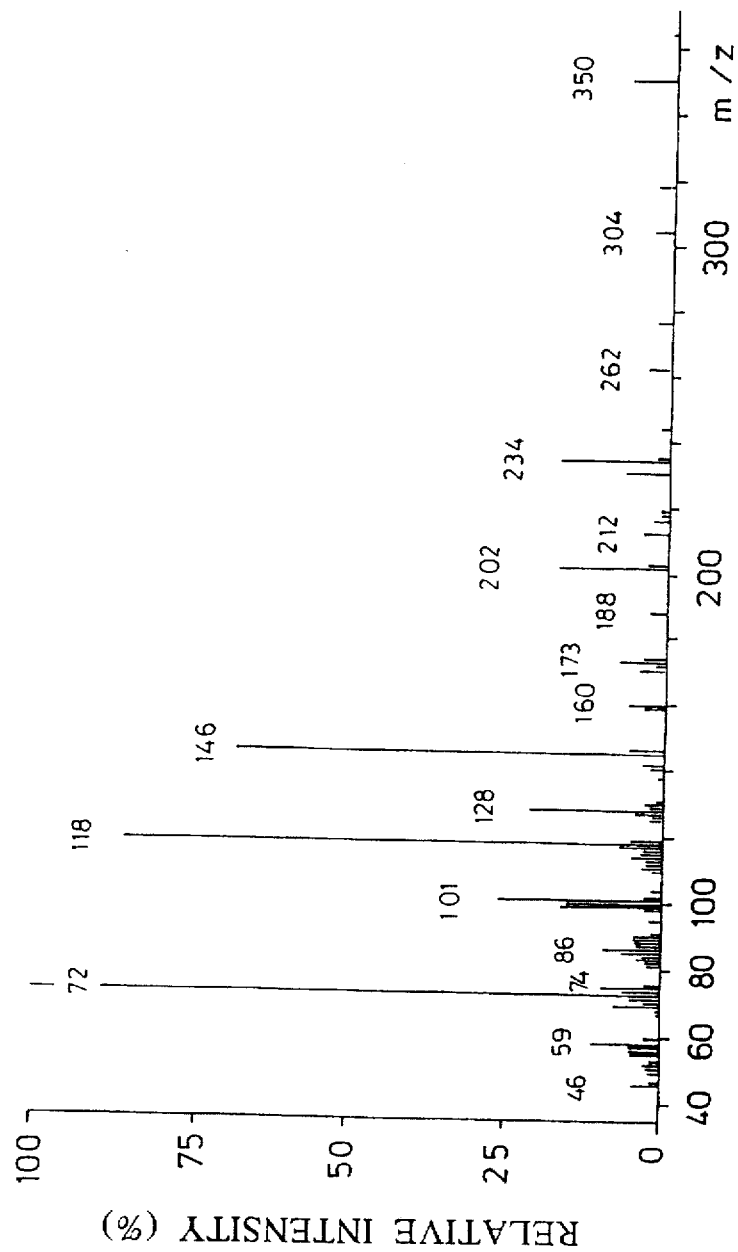

The linkage of the two heptoses (HepII-Hep I) together was determined by methylation analysis of the permethylated disaccharide 12. 1,3,5,-Tri-O-acetyl-2,4,6,7-tetra-O-methylheptitol (18, t$_R$=15.1 min, FIG. 10) was obtained, from which it was possible to determine the linkage of the heptoses together as Hepp-(1→3)-Hepp. The mass fragments (EI-MS) were at m/z=118, 234, 350 and were identified as fragments from the reducing end (FIG. 10). The data from the CI-MS analysis, |M+NH$_4$|$^+$ with m/z=413 and |M+H|$^+$ with m/z=396 are consistent with this interpretation.

On the other hand, carrying out the methylation analysis described above on the intact core oligosaccharide in place of the disaccharide revealed a 1,3,5-tri-O-acetyl-7-O-(N,N-dimethylcarbamoyl)-2,4,6-tri-O-methylheptitol 17 with a retention time of 24.5 min. The existence of a 3-O-acetylated 7-O-carbamoylheptitol in 17 can be explained by substitution of the GalN|Ala| residue in position 3 of Hep II in the intact core oligosaccharide. This result is consistent with data obtained earlier by Rowe and Meadow |Rowe, P. S. N. and Meadow, P. M., Eur. J. Biochem., 132 (1983) 329–337| and E. Altman et al. (E. Altman et al., Biochemistry 1994, submitted for publication; E. Altman et al., Int. Carb. Conference, Paris 1992, Abstract Book C161, p. 626; H. Masoud et al., 2nd Conference of the International Endotoxin Society (IES), Vienna 1992, 69, p. 55), who had determined the site of substitution of GalN-Ala and the linkage of the heptoses with one another likewise as GalpN |Ala|-(1→3)-LαD-Hepp-(1→3)-LαD-Hepp.

Figure 12A:
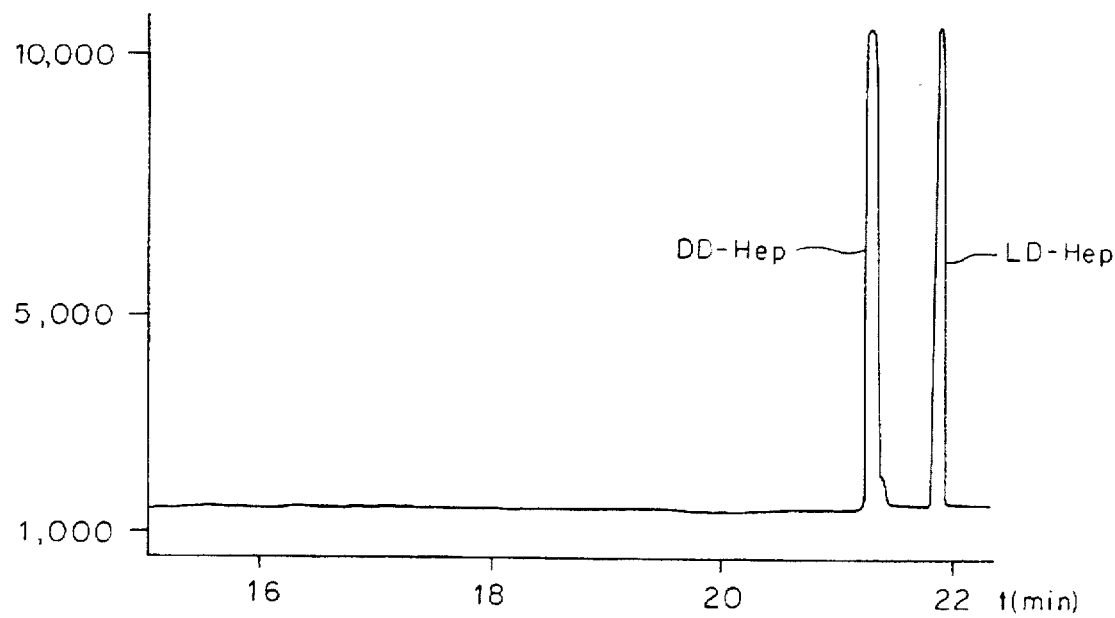
FIG. 12 shows the gas-liquid chromatogram (GC) of a standard of per-O-acetylated-D-glycero-D-manno-heptitol (D,D-Hep) and L-glycero-D-manno-heptitol (L,D-Hep) (top) compared with the heptitol acetates from Hep I and Hep II isolated from the core oligosaccharide of PAC605, after removal of the 7-O-carbamoyl group. Column: SPB-5™, 150° C.-3 min then 5°/min to 330° C.
Figure 12B:
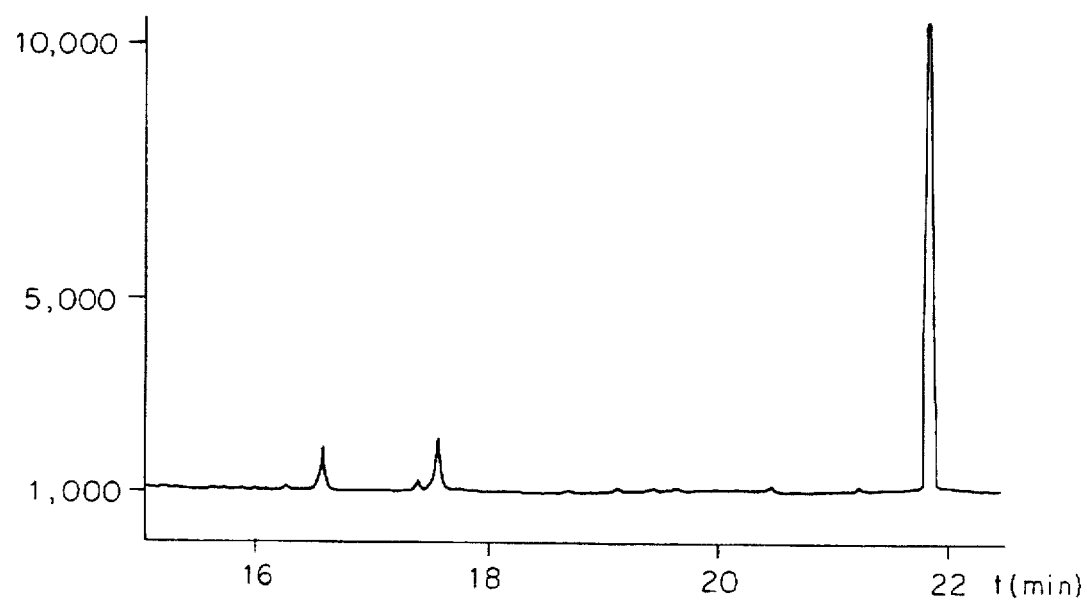

4.4. Assignment of the 7-O-carbamoylheptose to the L-glycero-D-manno or D-glycero-D-manno configuration Measured first in the GLC analysis (SPB-5®) was a standard which contained both peracetylated D-glycero-D-manno-heptitol (D,D-Hep-ol) and L-glycero-D-manno-heptitol (L,D-Hep-ol) (t$_R$=21.36 min, D,D-Hep:t$_R$=21.89 min, L,D-Hep). After the 7-O-carbamoyl radical on Hep II had been selectively removed from the core oligosaccharide of P. aeruginosa PAC605 by mild alkaline hydrolysis, the heptitol acetates prepared from Hep I and Hep II in this was were investigated in GC analysis. It emerged that only L-glycero-D-manno-heptitol acetate was detectable, t$_R$=21.89 min, which corresponds to L,D-Hep-ol (FIG. 12). This experiment and the fact that the heptose remains intact on elimination of the carbamoyl substituent made it probable that the 7-O-carbamoylheptopyranose (Hep II) has the L-glycero-D-mannoheptose configuration (compare also NMR analysis).

4.5 NMR analysis of the methyl-3-O-(7O-carbamoyl-L-glycero-α-D-manno-heptopyranosyl)-L-glycero-α-D-mannoheptopyranose 9α

4.5.1. $^1$H-NMR analysis

Figure 13A:
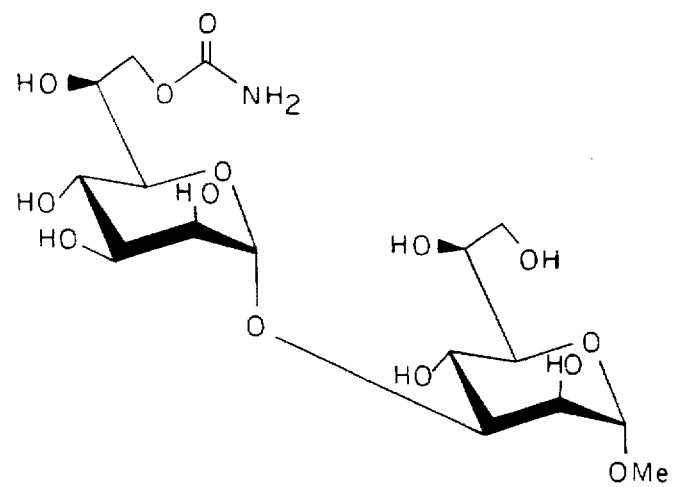
FIG. 13 shows the structural formula and the $^1$H-NMR spectrum of methyl-7-O-carbamoyl-LαD-Hepp-(1→3)-LαD-Hepp (1→OMe) (compound No. 9α) (360 MHZ, D$_2$O, room temperature).
Figure 13B:
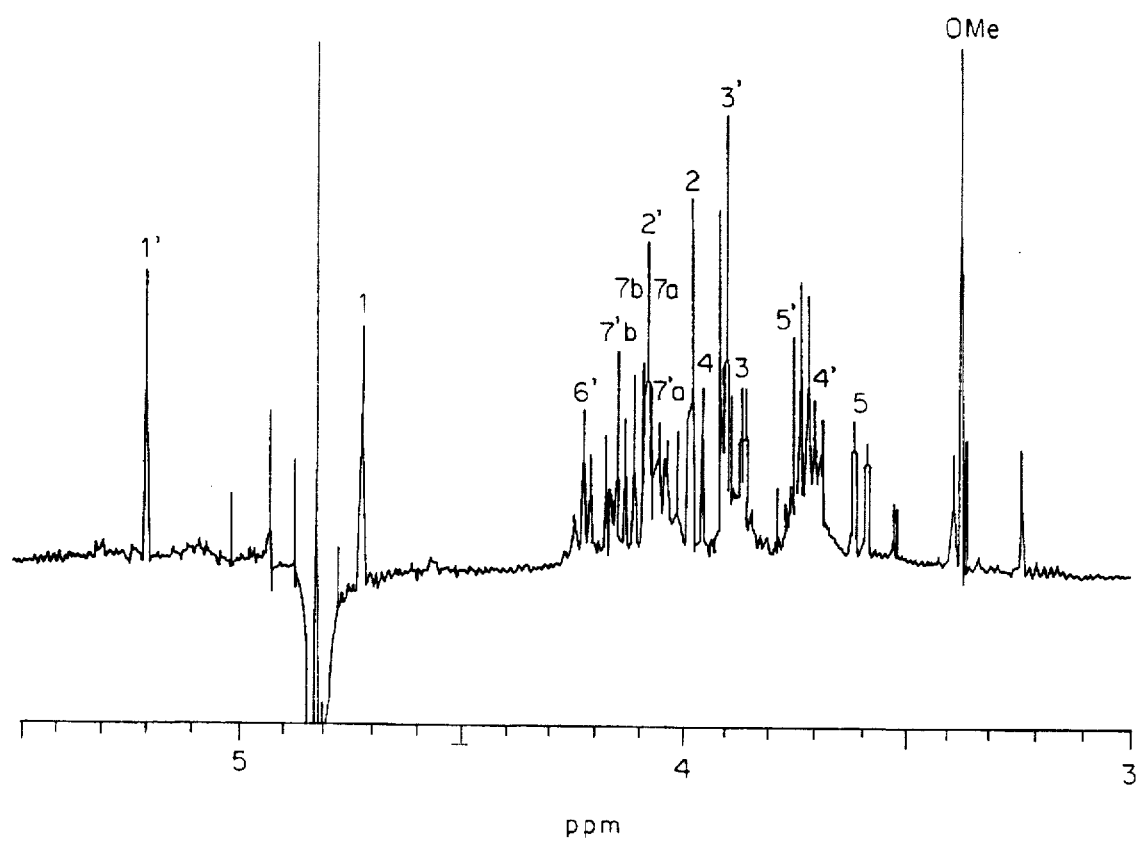

The disaccharide 3-O-(7-O-carbamoyl-L-glycero-α-D-manno-heptopyranoysl)-L-glycero-α-D-manno-heptopyranose 9α was isolated after mild methanolysis from the dephosphorylated core oligosaccharide and was purified by HPLC. The results of the proton NMR analysis are depicted in FIG. 13 and Table 1. It is significant that there is a low-field shift of the signals for H-7'a and H-7'b by about 0.3 ppm (4.085 and 4.154 ppm) in 7-O-carbamoylheptose compared with the analog signals for H-7a and H-7b in the unsubstituted heptose (3.7276 and 3.751 ppm respectively). Substitution in position 3 of Hep I is manifested only by a low-field shift of about 0.12 ppm compared with the α-anomeric methyl L-glycero-D-manno-heptopyranoside 2α. All the other signals agree well with the synthetic disaccharide methyl-3-O-(L-glycero-α-D-manno-heptopyranosyl)-L-glycero-α-D-manno-heptopyranose (10α). The good agreement of the signals is a further indication of the L-glycero-α-D-manno configuration found in the GC analysis.

4.5.2 $^{13}$C-NMR analysis of disaccharide 9α

Figure 14A:
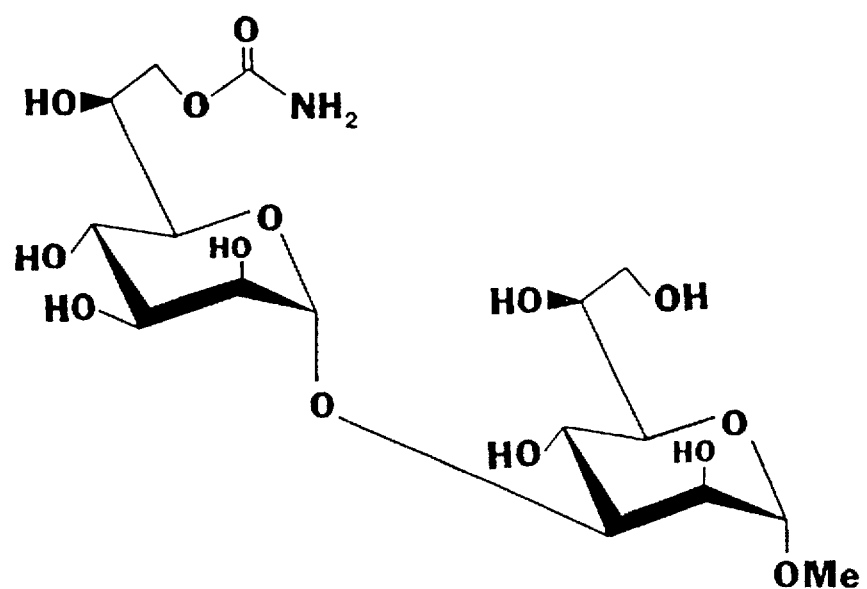
FIG. 14 shows the structural formula and the $^{13}$C—NMR spectrum of methyl-7-O-carbamoyl-LαD-Hepp-(1→3LαD-Hepp-(1→OMe) (compound No. 9α). (90 MHz, D$_2$O, room temperature).
Figure 14B:
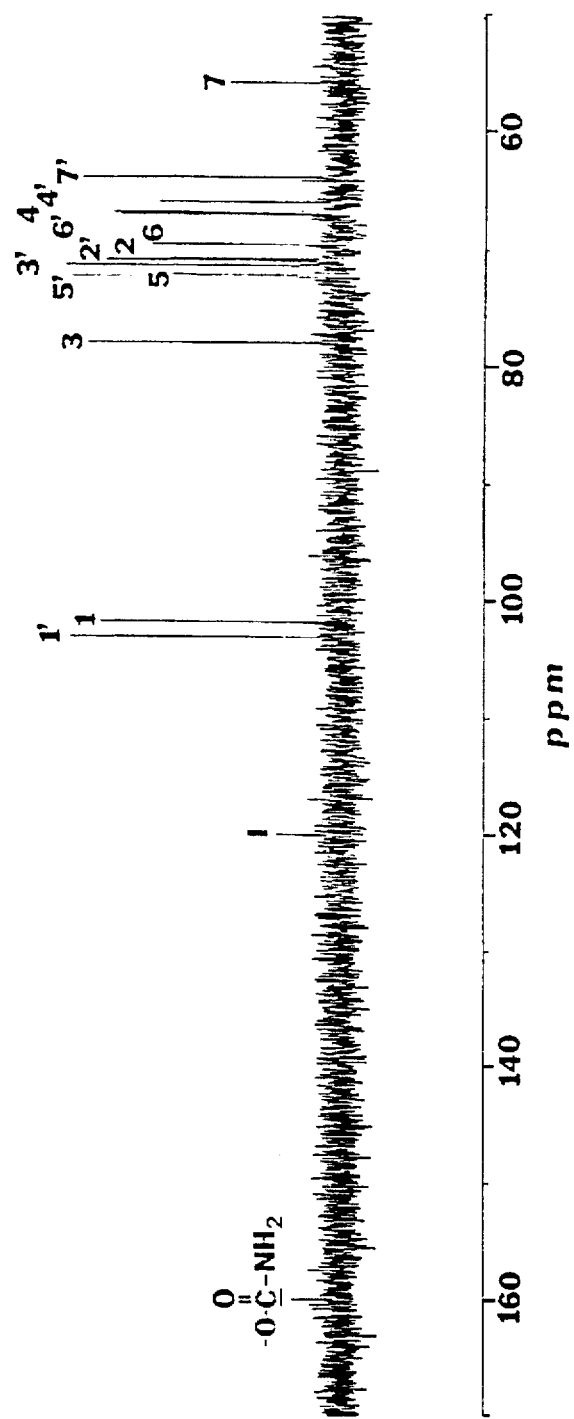

The results of the $^{13}$C-NMR analysis derived from the spectra with heteronuclear correlation for the disaccharide 3-O-(7-O-carbamoyl-L-glycero-α-D-manno-heptopyranosyl)-L-glycero-α-D-manno-heptopyranose (9α) are to be found in FIG. 14 and Table 2. Comparison with the synthetic disaccharide methyl-3-O-(L-glycero-α-D-manno-heptopyranosyl)-L-glycero-α-D-manno-heptopyranose (10α) and the synthetic monosaccharide methyl L-glycero-α-D-manno-heptopyranoside (2α) made it possible to deduce the individual structural features of the heptose (7-O-carbamoyl substitution, glycosidic linkage and configuration). The carbonyl CI—NH$_2$ signal at 159.86 ppm is particularly noteworthy and agrees well with an analog signal (159.6 ppm) for a 6-O-carbamoyl-GlcN(Me: 18:0)-R from *Azorhizobium caulinodans* which was recently described (Mergaert, P. et al., *Proc. Natl. Acad. Sci. USA*, 90 (1993) 1151–1555). The low-field shift of the signal for C-7' in 9α is only about 2.2 ppm by comparison with the unsubstituted compound 10α, which is not unusual for glycosidic substituents on primary hydroxyl groups. On the other hand, the low-field shift of C-3 on Hep I (71.35 vs. 77.89 ppm) is significant, which again confirms the Hep-(1→3)-Hep substitution in the disaccharide. All the other signals agree well with the disaccharide 10α. The good agreement of the $^{13}$C signals with the synthetic reference compounds 2α and 10α is a further indication of the L-glycero-α-D-manno configuration found in both heptoses.

4.6 Laser desorption mass analysis (LD-MS) of the methyl-3-O-(7-O-carbamoyl-L-glycero-α-D-manno-heptopyranosyl)-L-glycero-α-D-manno-heptopyranose 9α

Figures 15A, 15B:
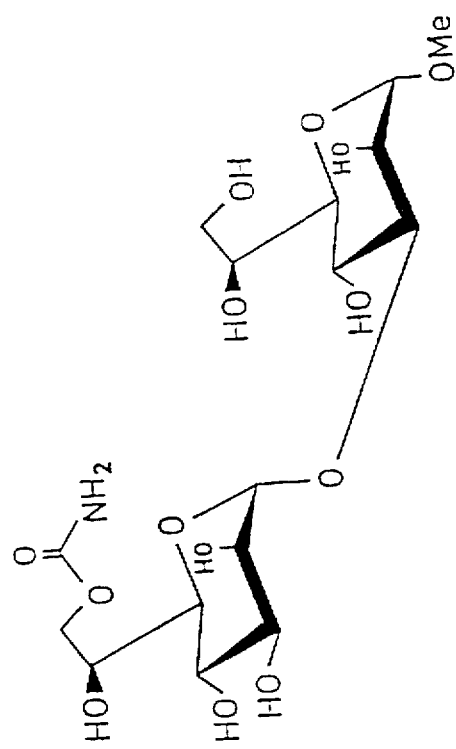
FIG. 15 shows the structural formula, the molecular formula and the laser desorption mass spectrum of methyl-7-O-carbamoyl-LαD-Hepp-(1→3θ-LαD-Hepp-(1→OMe) (compound No. 9α).
Figure 15C:
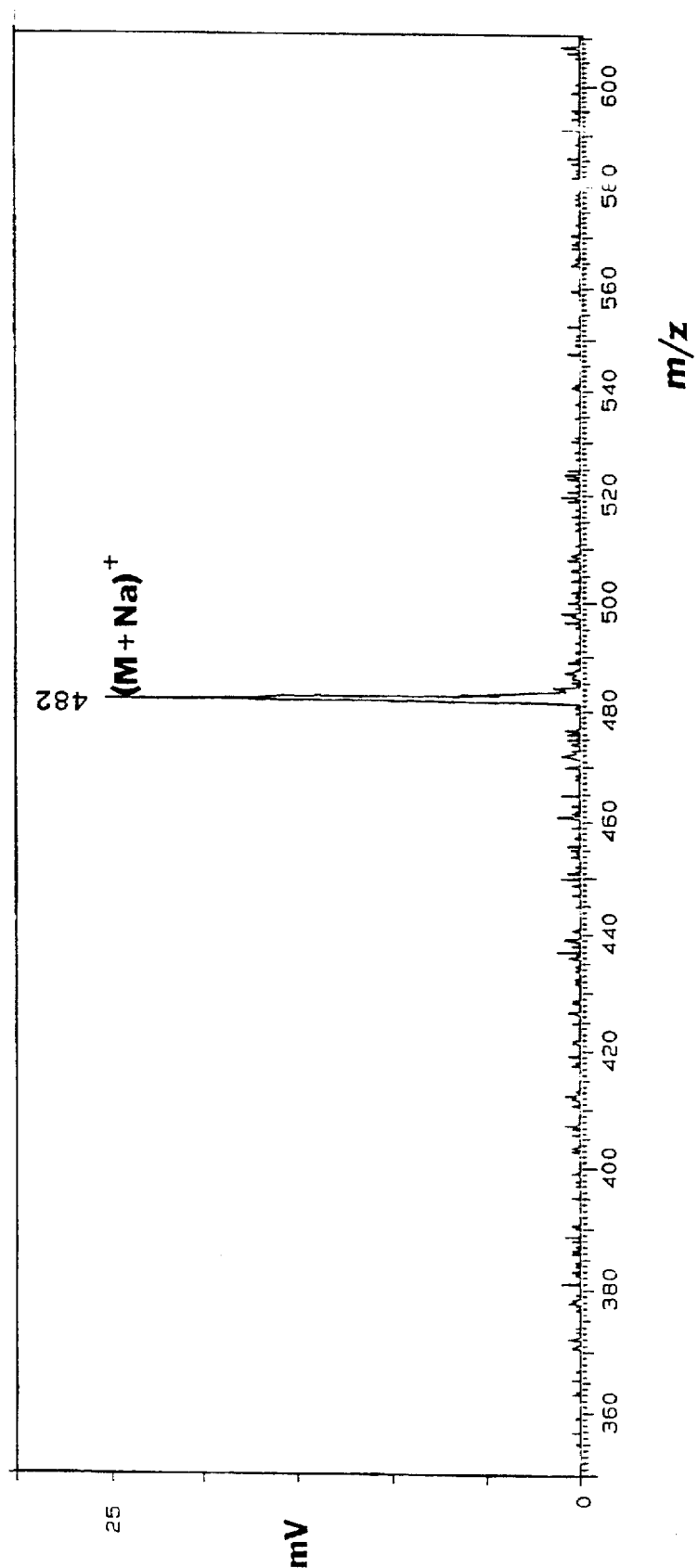

The result of the laser desportion mass analysis of compound 9α is depicted in FIG. 15. The molecular weight of the methyl-3-O-(7-O-carbamoyl-L-glycero-α-D-manno-heptopyranosyl)-L-glycero-α-D-heptopyranose (9α) was calculated for the molecular formula C$_{18}$O$_{14}$H$_{29}$N as 459.40. The LD-MS spectrum showed the purified disaccharide 9α as a unique pseudomolecular peak with a molar mass of |M+Na|$^+$=459+23=482 and is thus in excellent agreement with the calculated structure shown.

TABLE 1

Chemical shift, assignment and coupling constants for the signals in the $^1$H-NMR spectrum of methyl-7-O-carbamoyl-LαD-Hepp-(1→3)-LαD-Hepp-(1→OMe) 9α compared with the synthetic LαD-Hepp-(1→3)-LαD-Hepp-(1→OMe) 10α and LαD-Hepp-(1→OMe) 2α reference compounds (360 MHz, D$_2$O, room temperature).

| 7-O-carbamoyl-LαD-Hepp-(1→ 9α | | 10α | |
|---|---|---|---|
| | δ (ppm) | J (Hz) | δ (ppm) | J (Hz) |
| H-1' | 5.197 | 1.3 | 5.150 | 1.7 |
| H-2' | 4.093 | 2.6 | 4.071 | 3.1 |
| H-3' | 3.913 | 6.2 | 3.894* | |
| H-4' | 3.703 | 5.7 | 3.894* | 9.8 |
| H-5' | 3.709 | 1.3 | 3.705 | 1.9 |
| H-6' | 4.228 | 7.9 | 4.052 | 5.4 |
| H-7'a | 4.085 | 10.5 | 3.729 | 11.9 |
| H-7'b | 4.154 | 6.2 | 3.760 | 6.8 |

| →3)-LαD-Hepp-(1→OMe) | | | | 2α | |
|---|---|---|---|---|---|
| H-1 | 4.717 | 1.3 | 4.747 | 1.9 | 4.737 | 1.5 |
| H-2 | 3.983 | 3.5 | 4.031 | 3.2 | 3.895 | 3.4 |
| H-3 | 3.906 | 10.3 | 3.842 | 9.9 | 3.729 | 9.8 |
| H-4 | 3.983 | 9.7 | 3.967 | 10.0 | 3.825 | 10.2 |
| H-5 | 3.600 | 1.5 | 3.604 | 1.6 | 3.544 | 1.9 |
| H-6 | 4.055 | 6.8 | 4.048 | 5.8 | 4.015 | 5.8 |
| H-7a | 3.727 | 11.6 | 3.662 | 11.4 | 3.685 | 11.1 |
| H-7b | 3.751 | 6.9 | 3.741 | 7.4 | 3.731 | 7.3 |
| OMe | 3.370 | | 3.389 | | 3.380 | |

*unresolved multiplet

TABLE 2

Chemical shift and assignment of the $^{13}$C-NMR signals of 7-O-carbamoyl-LαD-Hepp-(1→3)-LαD-Hepp-(1→OMe) 9α, compared with synthetic reference compounds LαD-Hepp-(1→3)-LαD-Hepp-(1→OMe) 10α and LαD-Hepp-(1→OMe) 2α.

| | α (ppm) | |
|---|---|---|
| C atom | 9α<br>7-O-carbamoyl-LαD-Hepp-(1→ | 10α<br>LαD-Hepp-(1→ |
| C-1' | 103.06 | 103.30 |
| C-2' | 70.83 | 70.91 |
| C-3' | 71.33 | 71.35 |
| C-4' | 66.89 | 66.70 |
| C-5' | 72.09 | 72.63 |
| C-6' | 66.69 | 69.51 |
| C-7' | 65.90 | 63.68 |
| —O—CO—NH$_2$ | 159.86 | |

| | →3)-LαD-Hepp-OMe | →3)-LαD-Hepp-OMe | 2α<br>LαD-Hepp-OMe |
|---|---|---|---|
| C-1 | 101.77 | 101.75 | 103.30 |
| C-2 | 70.70 | 70.56 | 70.91 |
| C-3 | 77.89 | 70.09 | 71.35 |
| C-4 | 66.73 | 66.45 | 66.64 |
| C-5 | 72.26 | 72.04 | 72.04 |
| C-6 | 69.48 | 69.64 | 69.51 |
| C-7 | 63.73 | 63.68 | 63.68 |

*(D$_2$O, 90.556 MHz, ppm relative to internal acetonitrile 1.700 ppm)

TABLE 3

Identification of the 7-O-carbamoylheptose in the core oligosaccharide from various Gram-negative bacteria

| | 7-O-carbamoylheptopyranose |
|---|---|
| 1. Pseudomonadaceae (old classification) | |
| 1.1 Rough form mutants | |
| *Pseudomons aeruginosa* PAC605 | + |
| *P. aeruginosa* PAC 557 | + |
| *P. aeruginosa* PAC1R | + |
| *P. aeruginosa* RS (Habs 6) | + |
| 1.2. Smooth form bacteria | |
| *P. aeruginosa* Fischer 2 immunotype | + |
| *P. aeruginosa* Fischer 7 immunotype | + |
| *P. aeruginosa* 170519 | + |
| *P. aeruginosa* 170520 | + |
| *P. aeruginosa* FH-N-845 | + |
| *P. fluorescens* ATCC 49271 | + |
| Pseudomonas plantarii DSM 712B | – |
| 2. Non-Pseudamonadaceae | |
| Klebsiella pneumoniae, K 25 | – |
| Yersinis enterocolitica, mutant 490 M | – |
| Campylobacter jejuni RN16 O:58, CCUG 10936 | – |
| Proteus mirabilis mutant $R_{45}$ | – |
| Haemophilus influenzae, wild-type, Eagan strain | – |
| Vibrio parahaemolyticus, serotype O12 | – |
| Salmonella minnesota SF 1111 (S form) | – |
| Escherichia coli O111 (S form) | – |

We claim:

1. 7-O-Carbamoylheptose derivatives of the formula

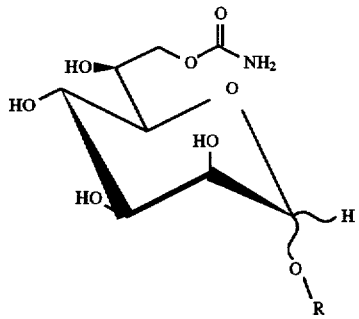

(I)

wherein R is $R^1$ or a group of the formula (II)

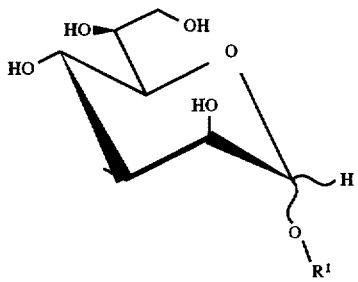

(II)

wherein $R^1$ is a hydrogen atom, a methyl group or a linker substituent suitable for covalent coupling.

2. 7O-Carbamoylheptose derivatives according to claim 1 wherein the linker substituent is a cysteamine residue, an allyl group or a straight-chain or branched-chain $C_{1-18}$ alkyl group which is unsubstituted or substituted with a hydroxyl, amino, acyl, carboxyl or allyl group.

3. 7O-Carbamoylheptose derivatives according to claim 1 wherein $R^1$ is a hydrogen atom or a methyl group.

4. Compositions for treating Pseudomonas infections comprising an effective amount of at least one carbamoylheptose derivative according to claim 1 in a pharmaceutically acceptable carrier.

5. A method for treating Pseudomonas infections comprising administering to a patient in need thereof an effective amount of at least one carbamoyheptose derivative according to claim 1.

6. A process for preparation of 7O-carbamoylheptose derivatives of the formula

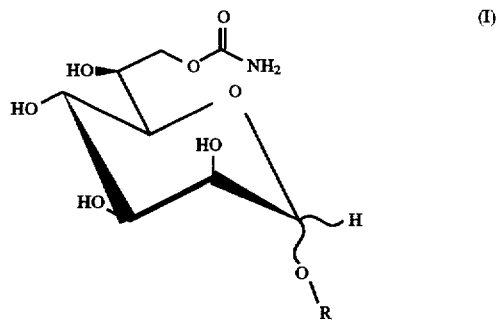

(I)

wherein R is $R^1$ or a group of the formula (II)

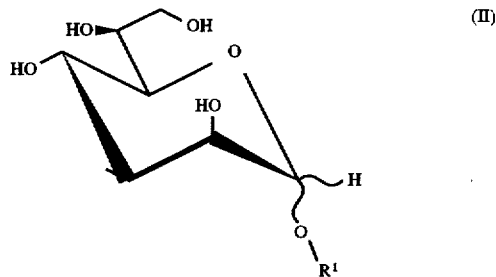

(II)

wherein $R^1$ is a hydrogen atom, a methyl group or a linker substituent suitable for covalent coupling; comprising:

(a) treating intact Gram-negative bacteria with hydrofluoric acid;

(b) hydrolyzing or metholyzing the treated bacteria to liberate heptose derivatives; and (c) permethylating the heptose derivatives.

* * * * *